(12) United States Patent
Kishimoto et al.

(10) Patent No.: US 12,427,147 B2
(45) Date of Patent: Sep. 30, 2025

(54) RETINAL GANGLION CELL DEATH INHIBITOR

(71) Applicant: SENJU PHARMACEUTICAL CO., LTD., Osaka (JP)

(72) Inventors: Yayoi Kishimoto, Osaka (JP); Chiho Yabuta, Osaka (JP)

(73) Assignee: SENJU PHARMACEUTICAL CO., LTD., Osaka (JP)

( * ) Notice: Subject to any disclaimer, the term of this patent is extended or adjusted under 35 U.S.C. 154(b) by 1080 days.

(21) Appl. No.: 17/289,201

(22) PCT Filed: Oct. 28, 2019

(86) PCT No.: PCT/JP2019/042107
§ 371 (c)(1),
(2) Date: Apr. 27, 2021

(87) PCT Pub. No.: WO2020/090705
PCT Pub. Date: May 7, 2020

(65) Prior Publication Data
US 2021/0346386 A1  Nov. 11, 2021

(30) Foreign Application Priority Data

Oct. 31, 2018  (JP) .................................. 2018-204891

(51) Int. Cl.
| | | |
|---|---|---|
| *A61K 31/00* | (2006.01) | |
| *A61K 31/4418* | (2006.01) | |
| *A61K 31/496* | (2006.01) | |
| *A61K 31/519* | (2006.01) | |
| *A61K 39/395* | (2006.01) | |
| *A61P 27/02* | (2006.01) | |
| *A61P 27/06* | (2006.01) | |
| *C07K 16/22* | (2006.01) | |
| *C07K 16/28* | (2006.01) | |

(52) U.S. Cl.
CPC ........ *A61K 31/519* (2013.01); *A61K 31/4418* (2013.01); *A61K 31/496* (2013.01); *A61P 27/02* (2018.01); *C07K 16/22* (2013.01); *C07K 16/2863* (2013.01); *C07K 2317/54* (2013.01); *C07K 2317/55* (2013.01); *C07K 2317/56* (2013.01); *C07K 2317/622* (2013.01); *C07K 2317/626* (2013.01)

(58) Field of Classification Search
CPC .. A61K 31/00; A61K 31/519; A61K 31/4418; A61K 31/496; A61K 2039/505; A61K 39/3955; A61P 27/02; A61P 27/06; C07K 16/22; C07K 16/2863
See application file for complete search history.

(56) References Cited

U.S. PATENT DOCUMENTS

| | | |
|---|---|---|
| 2005/0118585 A1 | 6/2005 | Clark et al. |
| 2010/0093760 A1* | 4/2010 | Yu ............................ A61P 43/00 435/375 |
| 2010/0292454 A1* | 11/2010 | Mishina .................. A61P 25/06 536/24.5 |
| 2013/0089560 A1* | 4/2013 | Chartier-Courtaud ...................... C07K 16/2896 435/375 |
| 2015/0030572 A1 | 1/2015 | Zack et al. |
| 2015/0050360 A1* | 2/2015 | Tan ....................... C12Q 1/6886 424/649 |
| 2015/0376625 A1* | 12/2015 | Oestergaard ....... C12N 15/1138 536/24.5 |
| 2018/0162932 A1 | 6/2018 | Krishnadath et al. |
| 2018/0355319 A1 | 12/2018 | Yamamoto et al. |

FOREIGN PATENT DOCUMENTS

| | | | |
|---|---|---|---|
| JP | 2005-518788 A | 6/2005 | |
| JP | 2017-537603 A | 12/2017 | |
| WO | WO-2007123402 A2 * | 11/2007 | ........... A61K 38/185 |
| WO | WO-2008030611 A2 * | 3/2008 | ........... A61K 39/395 |
| WO | WO-2010114860 A1 * | 10/2010 | ............ A61K 38/00 |
| WO | WO 2015/054526 A2 | 4/2015 | |
| WO | WO 2015/054526 A3 | 4/2015 | |
| WO | WO 2016/032263 A1 | 3/2016 | |
| WO | WO 2017/026462 A1 | 2/2017 | |

OTHER PUBLICATIONS

Agarwal et al. An update on inflammatory choroidal neovascularization: epidemiology, multimodal imaging, and management. J Ophthal Inflamm Infect 8: 13, 2018 (18 total pages).*
Belforte et al. Metabolic stress in glaucoma engages early activation of the energy biosensor AMPK leading to neuronal dysfunction. Investigat Ophthalmol Vis Sci 58: 2958, 2017.*
Calpe et al. Effective Inhibition of Bone Morphogenetic Protein Function by Highly Specific Llama-Derived Antibodies. Mol Cancer Ther 14(11): 2527-2540, 2015.*
Conley et al. Nanoparticles for retinal gene therapy. Prog Retinal Eye Res 29: 376-397, 2010.*
Hoorbakht et al. Optic Neuritis, its Differential Diagnosis and Management. Open Ophthalmol J 6: 65-72, 2012.*
Bhattacharya et al. Impact of genetic variation on three dimensional structure and function of proteins. PLoS One 12(3): e0171355, 2017.*
Bork, P. Powers and pitfalls in sequence analysis: the 70% hurdle. Genome Res 10: 398-400, 2000.*

(Continued)

*Primary Examiner* — Bridget E Bunner
(74) *Attorney, Agent, or Firm* — Leydig, Voit & Mayer, Ltd.

(57) ABSTRACT

The present invention relates to a retinal ganglion cell death suppressor comprising a BMPR signal transduction inhibitor, a drug comprising a BMPR signal transduction inhibitor for protecting retinal neurons, and a pharmaceutical composition using these for preventing or treating a disease involving retinal ganglion cell death, such as glaucoma, diabetic retinopathy and retinal vascular occlusion.

15 Claims, 4 Drawing Sheets

(56) References Cited

OTHER PUBLICATIONS

Bork, P. Go hunting in sequence databases but watch out for the traps. Trends in Genetics 12(10): 425-427, 1996.*
Brenner. S.E. Errors in genome annotation. Trends in Genetics 15:132-133, 1999.*
Deng et al. BMP4 promotes hepatocellular carcinoma proliferation by autophagy activation through JNK1-mediated Bcl-2 phosphorylation. J Exp Clin Cancer Res 37: 156, 2018 (plus supplemental information materials) (18 total pages).*
Doerks et al. Protein annotation: detective work for function prediction. Trends in Genetics 14:248-250, 1998.*
Fenton et al. Rheostat positions: a new classification of protein positions relevant to pharmacogenomics. Medicinal Chem Res 29: 1133-1146, 2020.*
Lagenfeld et al. Bone Morphogenetic Protein Type I Receptor Antagonists Decrease Growth and Induce Cell Death of Lung Cancer Cell Lines. PLoS One 8(4): e61256, 2013 (15 total pages).*
Lieven et al. Retinal Ganglion Cell Axotomy Induces an Increase in Intracellular Superoxide Anion. Invest Ophthalmol Vis Sci 47: 1477-1485, 2006.*
Liu et al. Bone Morphogenetic Protein 4 (BMP4): A Regulator of Capsule Chondrogenesis in the Developing Mouse Inner Ear. Dev Dynamics 226: 427-438, 2003.*
Murakami et al. Regulatory expression of genes related to metastasis by TGF-B and activin A in B16 murine melanoma cell. Mol Biol Rep 37: 1279-1286, 2010.*
Raffaele et al. Compared antioxidant activity among corticosteroids on cultured retinal pigment epithelial cells. Grafes Arch Clin Exp Ophathalmol 254: 2411-2416, 2016.*
Roggia et al. Characterization of retinal pigment epithelial cells in rd1 mouse model of retinal degeneration. Invest Ophthalmol Vis Sci 56: 3642, 2015 (2 pages).*
Skolnick et al. From genes to protein structure and function: novel applications of computational approaches in the genomic era. Trends Biotechnol 18(I):34-39 2000.*
Smith et al. The challenges of genome sequence annotation or "the devil is in the details". Nature Biotechnol 15: 1222-1223, 1997.*
Sorescu et al. Bone Morphogenic Protein 4 Produced in Endothelial Cells by Oscillatory Shear Stress Induces Monocyte Adhesion by Stimulating Reactive Oxygen Species Production From a Nox1-Based NADPH Oxidase. Circ Res 95: 773-779, 2004.*
Tokuriki et al. Stability effects of mutations and protein evolvability. Curr Opin Structural Biol 19: 596-604, 2009.*
White et al. Menadione-treated synaptosomes as a model for post-ischaemic neuronal damage. Biochem J 253: 425-433, 1988.*
Yu et al. Bone Morphogenetic Protein (BMP) Type II Receptor Deletion Reveals BMP Ligand-specific Gain of Signaling in Pulmonary Artery Smooth Muscle Cells. J Biol Chem 280(26): 24443-24450, 2005.*
Sluch et al., "Enhanced Stem Cell Differentiation and Immunopurification of Genome Engineered Human Retinal Ganglion Cells," *Stem Cells Transl. Med.*, 6(11): 1972-1986 (2017).
European Patent Office, Extended European Search Report in European Patent Application No. 19879493.5 (Oct. 11, 2022).
Belforte et al., "Metabolic stress in glaucoma engages early activation of the energy biosensor AMPK leading to neuronal dysfunction," *ARVO Annual Meeting Abstract, Invest. Ophthalmol. Vis. Sci.*, 58(8): 2958 (Jun. 2017).
Hussein et al., "BMP2 and 4 Contribute to Retinal Endothelial Cell Barrier Dysfunction in Diabetic Retinopathy: Role of p38 MAPK Pathway," *ARVO Annual Meeting Abstract, Invest. Ophthalmol. Vis. Sci.*, 57(12): 5448 (Sep. 2016).
Ueki et al., "Activation of BMP-Smad1/5/8 Signaling Promotes Survival of Retinal Ganglion Cells after Damage In Vivo," *PLoS One*, 7(6): e38690 (2012).
Ying et al., "Metformin inhibits ALK1-mediated angiogenesis via activation of AMPK," *Oncotarget*, 8(20): 32794-32806 (2017).
Japanese Patent Office, International Search Report in International Patent Application No. PCT/JP2019/042107 (Nov. 26, 2019).

* cited by examiner

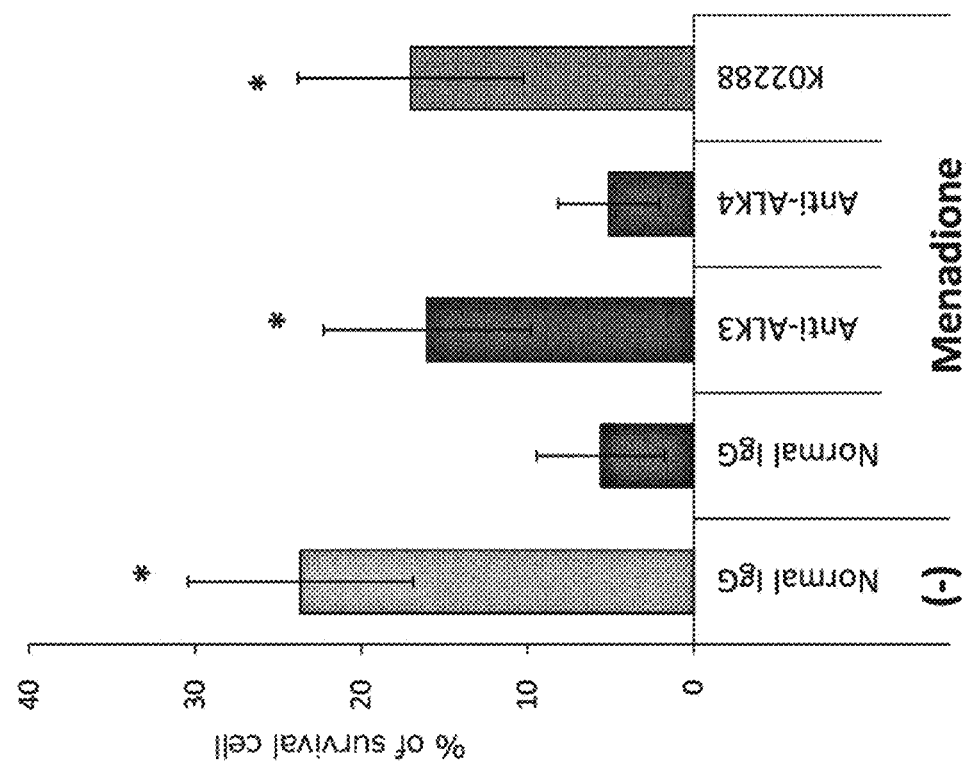
FIG. 1A  FIG. 1B  FIG. 1C
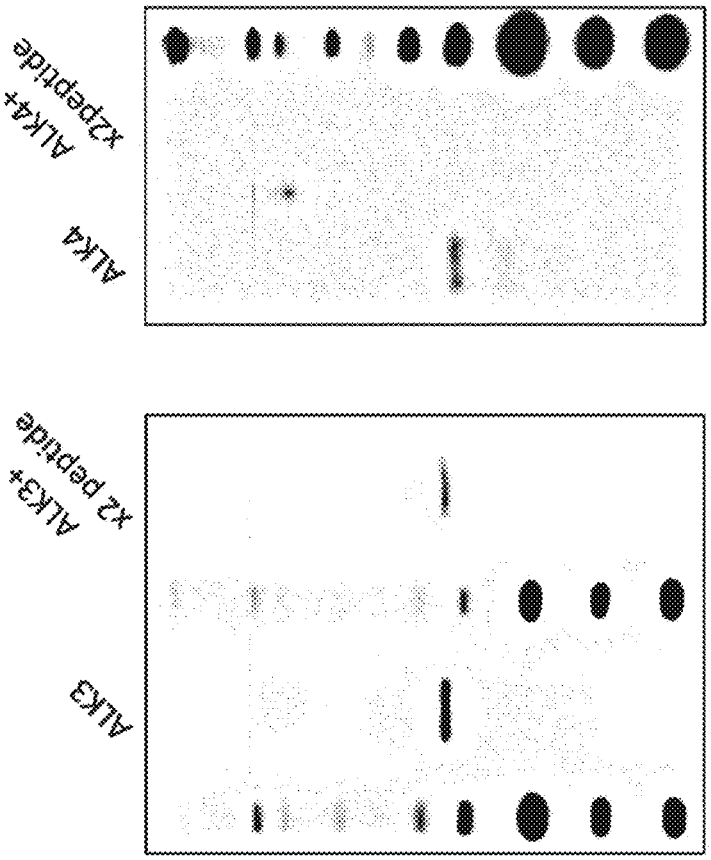

RETINAL GANGLION CELL DEATH INHIBITOR

CROSS-REFERENCE TO RELATED APPLICATIONS

This patent application is the U.S. national phase of International Patent Application No. PCT/JP2019/042107, filed Oct. 28, 2019, which claims the benefit of Japanese Patent Application No. 2018-204891, filed on Oct. 31, 2018, which are incorporated by reference in their entireties herein.

TECHNICAL FIELD

Related Application

The specification incorporates the contents disclosed in the specification of Japanese Patent Application No. 2018-204891 (file on Oct. 31, 2018) which is the basis for the priority of the present application.

Technical Field

The present invention relates to suppression of retinal ganglion cell death and prevention or treatment for a disease involving retinal ganglion cell death, using a BMPR (BMP receptor) signal transduction inhibitor.

BACKGROUND ART

Glaucoma is a progressive disease having a characteristic change in the optic nerve and field of view, and a cause of weakening eyesight and vision loss. Although the onset mechanism of glaucoma is not sufficiently elucidated, retinal ganglion cell death is considered as one of the causes. The retinal ganglion cell death is considered to be caused by, e.g., intracellular depletion of nutrients and oxidative stress due to elevation of intraocular pressure. Not only glaucoma but also ophthalmic diseases causing vision loss and weakening eyesight often have retinal ganglion cell death as a pathological condition.

Ueki et al., analyzed signal transduction of bone morphogenetic protein (BMP) in the mouse retina and have reported that retinal ganglion cell death induced by NMDA is suppressed by a kind of BMP, i.e., BMP4, and that the cell death is accelerated by a BMP inhibitor (Noggin) (Non Patent Literature 1). Clark et al., analyzed expression of BMP gene in the human ocular tissue and found that the expression level of a BMP antagonist, i.e., gremlin, increases in the trabecular meshwork endothelial cells of a subject affected with glaucoma. Based on this, they have reported the possibilities of diagnosis for glaucoma based on BMP-gene expression and treatment for glaucoma by use of a BMP agonist (Patent Literature 1).

As mentioned above, the reports regarding BMP up to present have suggested that activation of the BMP signal transduction system may suppress retinal ganglion cell death (Patent Literature 1 and Non Patent Literature 1).

CITATION LIST

Patent Literature

Patent Literature 1: Japanese Translation of PCT International Application Publication No. 2005-518788

Non Patent Literature

Non Patent Literature 1: Yumi Ueki, Thomas A. Reh, "Activation of BMP-Smad1/5/8 Signaling Promotes Survival of Retinal Ganglion Cells after Damage In Vivo" PLoS ONE, June 2012, Volume 7, Issue 6, e38690

SUMMARY OF INVENTION

An object of the present invention is to elucidate a mechanism that induces retinal ganglion cell death and provide a novel means for protecting the retinal neurons and a means for preventing or treating a disease involving retinal ganglion cell death, based on the elucidation.

The inventors found that retinal ganglion cell death is suppressed by inhibiting the BMPR signal transduction system ("BMPR", which will be also referred to as a "BMP receptor" herein), unlike the reports up to present.

More specifically, the present invention relates to the following (1) to (21).

(1) A retinal ganglion cell death suppressor comprising a BMPR signal transduction inhibitor.

(2) The retinal ganglion cell death suppressor according to (1), wherein the BMPR signal transduction inhibitor is an ALK3 signal transduction inhibitor.

(3) The retinal ganglion cell death suppressor according to (1), wherein the BMPR signal transduction inhibitor is any one selected from the group consisting of an anti-ALK3 antibody or a fragment thereof, an anti-BMP4 antibody or a fragment thereof, Dorsomorphin (6-[4-(2-piperidin-1-ylethoxy)phenyl]-3-pyridin-4-ylpyrazolo[1,5-a]pyrimidine), LDN-193189 (4-[6-(4-piperazin-1-yl-phenyl)-pyrazolo[1,5-α]pyrimidin-3-yl]-quinoline), 2-(3-(6-methylpyridin-2-yl)-1H-pyrazol-4-yl)-1,5-naphthyridine, K02288 (3-[6-amino-5-(3,4,5-trimethoxyphenyl)-3-pyridinyl]-phenol), DMH-1 (4-[6-[4-(1-methylethoxy)phenyl] pyrazolo[1,5-α]pyrimidin-3-yl]-quinoline), LDN-212854 (5-(6-(4-(1-piperazinyl)phenyl)pyrazolo[1,5-α]pyrimidin-3-yl)quinoline), LDN-214117 (1-[4-[6-methyl-5-(3,4,5-trimethoxyphenyl)-3-pyridinyl]phenyl] piperazine), and ML347 (5-[6-(4-methoxyphenyl)pyrazolo[1,5-a]pyrimidin-3-yl]quinoline).

(4) The retinal ganglion cell death suppressor according to (3), wherein the fragment is a fragment having a complementarity determining region (CDR) which specifically recognizes and binds to a target antigen, and e.g., an element selected from the group consisting of Fab, F(ab')$_2$, Fv, scFv, scFv-Fc, minibody and diabody.

(5) A retinal neuroprotective agent comprising the retinal ganglion cell death suppressor according to any one of (1) to (4).

(6) A pharmaceutical composition comprising the retinal ganglion cell death suppressor according to any one of (1) to (4), for preventing or treating a disease involving retinal ganglion cell death.

(7) The pharmaceutical composition according to (6), wherein the disease involving retinal ganglion cell death is any one or more selected from the group consisting of glaucoma, diabetic retinopathy, retinal vascular occlusion, ischemic optic neuropathy, a disease associated with choroidal neovascularization, Leber disease, dominant hereditary optic atrophy, optic neuritis and aniridia.

(8) A retinal cell transplantation adjuvant comprising the retinal ganglion cell death suppressor according to any one of (1) to (4).

(9) A method for culturing retinal cells, comprising culturing retinal cells (for example, retinal cells for transplantation) in the presence of the retinal ganglion cell death suppressor according to any one of (1) to (4).

(10) A method for suppressing retinal ganglion cell death, comprising the following step (a) or (b):
  (a) administering an effective amount of a BMPR signal transduction inhibitor to a subject in need of the suppression; or
  (b) culturing retinal ganglion cells in the presence of an effective amount of a BMPR signal transduction inhibitor.

(11) The method according to (10), wherein the BMPR signal transduction inhibitor further has characteristic(s) according to any one or more of (2) to (4).

(12) A method for protecting retinal neurons, comprising the following step (a) or (b):
  (a) administering an effective amount of a BMPR signal transduction inhibitor to a subject in need of the protection; or
  (b) culturing retinal neuron in the presence of an effective amount of a BMPR signal transduction inhibitor.

(13) The method according to (12), wherein the BMPR signal transduction inhibitor further has characteristic(s) according to any one or more of (2) to (4).

(14) A method for preventing or treating a disease involving retinal ganglion cell death, comprising a step of administering an effective amount of a BMPR signal transduction inhibitor to a subject in need of the prevention or treatment.

(15) The method according to (14), wherein the BMPR signal transduction inhibitor further has characteristic(s) according any one or more of (2) to (4).

(16) The method according to (14) or (15), wherein the disease involving retinal ganglion cell death is the disease according to (7).

(17) A BMPR signal transduction inhibitor for use in suppression of retinal ganglion cell death.

(18) The inhibitor according to (17), wherein the BMPR signal transduction inhibitor further has characteristic(s) according to any one or more of (2) to (4).

(19) The inhibitor according to (17) or (18), for use in protection of retinal neurons.

(20) The inhibitor according to any one of (17) to (19), for use in prevention or treatment of the disease involving retinal ganglion cell death.

(21) The inhibitor according to (20), wherein the disease involving retinal ganglion cell death further has the characteristic according to (7).

Advantageous Effects of Invention

The present invention allows effectively suppress retinal ganglion cell death and effectively protect retinal neurons. This will enable to provide a novel method for preventing and treating a disease involving retinal ganglion cell death, such as a serious eye disease leading to vison loss, for example, glaucoma, diabetic retinopathy and retinal vascular occlusion.

BRIEF DESCRIPTION OF DRAWINGS

FIGS. 1A and 1B show the confirmation results of specificities of an anti-ALK3 antibody and an anti-ALK4 antibody used in Examples, respectively. FIG. 1A shows Size marker; Sample reacted with anti-ALK3 antibody alone; Size marker; and Sample reacted with anti-ALK3 antibody and ALK3 peptide; in this order from the left. FIG. 1B shows Sample reacted with anti-ALK4 antibody alone; Sample reacted with anti-ALK4 antibody and ALK4 peptide; and Size marker, in this order from the left. FIG. 1C shows the effect of a BMPR signal transduction inhibitor on retinal ganglion cell death induced by menadione. The vertical axis represents the ratio (%) of the number of survival cells relative to the total number of cells; whereas the horizontal axis represents test samples: Control group (menadione−, Normal rabbit IgG+); Group treated with Normal IgG (menadione+ and Normal rabbit IgG+); Group treated with an anti-ALK3 antibody (menadione+ and anti-ALK3 antibody+); Group treated with an anti-ALK4 antibody (menadione+ and anti-ALK4 antibody+); and Group treated with K02288 (menadione+ and K02288+), in this order from the left. *$P<0.05$ Student's t-test vs Normal IgG treatment group, n=3.

DESCRIPTION OF EMBODIMENTS

Figure 2A:
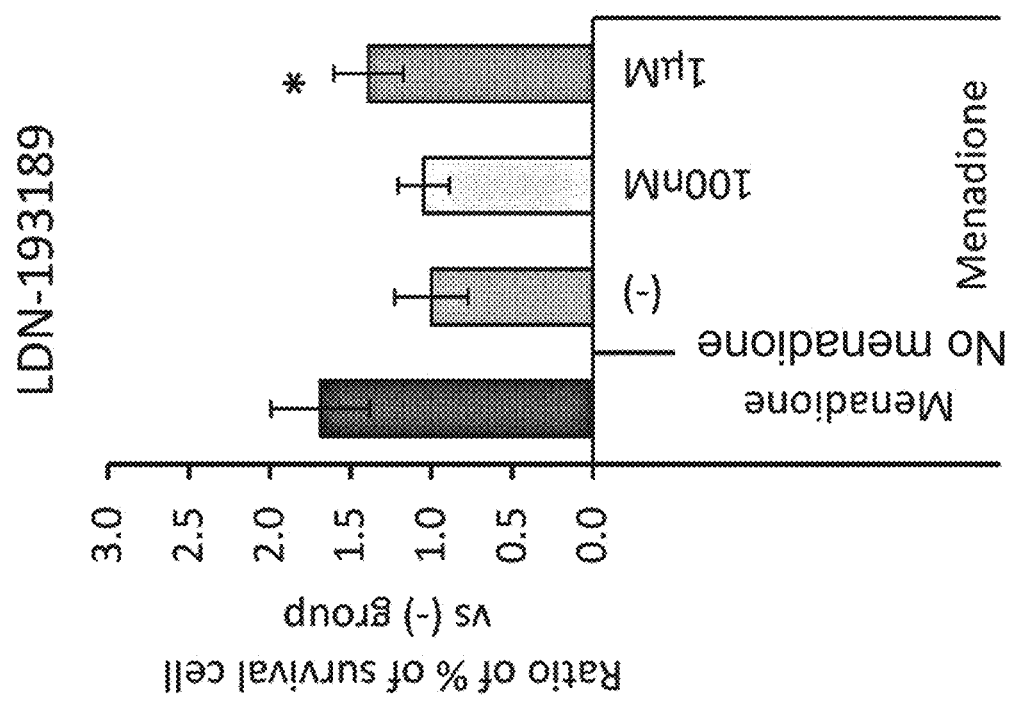
FIG. 2A shows the effect of a BMPR signal transduction inhibitor K02288 on retinal ganglion cell death induced by menadione. The vertical axis represents the ratio (%) of the number of survival cells relative to that of a group treated with menadione alone; whereas, the horizontal axis represents test samples: Control group (menadione−), Group treated with menadione alone; Group treated with 100 nM K02288; Group treated with 1 μM K02288; and Group treated with 10 μM K02288, in this order from the left. *$P<0.05$ Dunnett's test vs a group treated with menadione alone, n=8.

According to the present invention, a BMPR signal transduction inhibitor is used as an active ingredient in suppression of retinal ganglion cell death, protection of retinal neurons or prevention or treatment for a disease involving retinal ganglion cell death.

1. BMPR Signal Transduction Inhibitor

The BMPR signal transduction inhibitor according to the present invention refers to a substance that inhibits BMPR signal transduction via interaction between BMP and BMPR. The BMPR signal transduction inhibitor may have a function as a BMP signal transduction inhibitor.

BMPs are a group of proteins belonging to the TGF β super family. BMP, which was identified as a molecule inducing or promoting differentiation into bone and cartilage, has been known to play an important role in proliferation of cells, differentiation and control of apoptosis similarly to other molecules of the TGF β super family. A BMPR (receptor for BMP) is present on the surface of various types of cells. When BMP binds as a ligand to a BMPR, a signal is transmitted into the nucleus. Examples of ligands in the BMPR signal transduction pathway so far known include BMP2, BMP4, BMP5, BMP6, BMP7, BMP8A, BMP8B, BMP9, BMP10, GDF5, GDF6 and GDF7. The BMP family can be divided into subfamilies of BMP2/4, BMP5/6/7/8 (Osteogenic Protein-1 (OP-1)), BMP9/10 and GDF5/6/7. BMP2/4 includes BMP2 and BMP4; BMP5/6/7/8 (Osteogenic Protein-1 (OP-1)) includes BMP5, BMP6, BMP7, BMP8A, and BMP8B; BMP9/10 includes BMP9 and BMP10 and GDF5/6/7 includes GDF5, GDF6 and GDF7.

BMPR is a serine/threonine kinase receptor and has a BMP type-I receptor and a BMP type-II receptor (hereinafter, refer to as "type-I receptor" and "type-II receptor", respectively). Examples of the Type-I receptor so far known include, activin receptor-like kinase (ALK)1 (ACVRL1, SKR3), ALK2 (ACVR1, ACTRI), ALK3 (BMPR1A) and ALK6 (BMPR1B). Examples of the Type II receptor so far known include BMPR2, ACTRIIA and ACTRIIB. (Note that, alternative name(s) is/are shown within parentheses).

For signal transduction by BMPR, it is necessary that two Type-I receptor molecules and two Type II receptor molecules form a hetero-tetramer and it binds to BMP serving as a ligand. Examples of the binding mode between the hetero-tetramer and a ligand, are as follows: Type-I receptors and Type II receptors form a hetero-tetramer, and then, a ligand binds; and a Type-I receptor and a ligand first bind, and then, a Type II receptor is recruited. When the hetero-tetramer binds to a ligand, signal transduction by BMPR is activated; however, it is suggested that the signal transduction pathway varies depending on the binding mode. The SMAD pathway via a SMAD protein is known for signal transduction by BMPR. For example, BMPR binds to BMP, migrates into a cell and phosphorylates SMAD1/5/8 by the activation of a kinase. The SMAD molecule phosphorylated forms a complex with SMAD4, migrates into the nucleus and serves as a transcriptional regulator to control gene expression. As a BMPR signal transduction pathway other than the SMAD pathway, a non-SMAD pathway not mediated by a SMAD molecule is known (Tian X Y et al., J Mol Cell Cardiol. 2012 January; 52 (1): 237-44).

The BMPR signal transduction inhibitor of the present invention acts anywhere in the BMPR signal transduction pathway mentioned above to inhibit signal transduction mediated by BMP and BMPR. Accordingly, examples of the BMPR signal transduction inhibitor of the present invention include, but are not limited to:

(1) substances that block or inhibit binding of BMP to BMPR: for example, a BMPR antagonist and antagonist antibody (neutralizing antibody), an anti-BMPR antibody, a BMP antagonist and antagonist antibody (neutralizing antibody), an anti-BMP antibody, a dominant negative BMP and a dominant negative BMPR;

(2) substances that suppress expression of BMP and BMPR: for example, substances that inhibit transcription of BMP and BMPR genes, substances that inhibit processing of an early transcript into mRNA, substances that inhibit transport of mRNA into the cytoplasm, substances that promote decomposition of mRNA, substances that inhibit translation of mRNA into a protein, substances that inhibit post-translational modification of a protein, and preferably, antisense nucleic acids or small interfering RNA (siRNA) to mRNA of BMP or BMPR;

(3) substances that block or inhibit intracellular signal transduction: for example, a SMAD1/5/8 pathway inhibitor, dominant negative form of each SMAD molecule, inhibitory SMAD that inhibits migration of SMAD4 into the nucleus, a non-SMAD pathway inhibitor and an inhibitor of a molecule (for example, Tak1, Tab1) involved in the non-SMAD pathway; and (4) substances that suppress expression of molecules involved in intracellular signal transduction: for example, substances that inhibit transcription of each of SMAD genes, Tak1 gene and Tab1 gene, substances that inhibit processing of an early transcript into mRNA, substances that inhibit transfer of mRNA into the cytoplasm, substances that promote decomposition of mRNA, substances that inhibit translation of mRNA into a protein, substances that inhibit post-translational modification of a protein, preferably, antisense nucleic acids or siRNA to mRNA of each of SMAD molecules, Tak1 molecule, or Tab1 molecule.

The BMPR signal transduction inhibitor of the present invention may be a protein such as an antibody, a nucleic acid molecule such as an antisense nucleic acid and siRNA, and a low-molecular weight compound.

Examples of the protein that can be used as the BMPR signal transduction inhibitor of the present invention include naturally occurring molecules such as Noggin, Chordin, Follistatin, Cerberus and Gremlin, anti-BMP antibodies (particularly, an anti-BMP4 antibody), antagonist antibodies such as anti-BMPR antibodies (preferably, anti-ALK3 antibody), dominant negative forms of BMP (preferably, dominant negative form of BMP4) and dominant negative forms of BMPR (preferably, dominant negative form of ALK3).

Examples of the nucleic acid molecule that can be used as the BMPR signal transduction inhibitor of the present invention include antisense nucleic acids or siRNA to mRNAs of BMP4, ALK3, SMAD1/5/8, SMAD4, Tak1 or Tab1.

Examples of the low-molecular weight compound that can be used as the BMPR signal transduction inhibitor of the present invention include Dorsomorphin (6-[4-(2-piperidin-1-ylethoxy)phenyl]-3-pyridin-4-ylpyrazolo[1,5-a]pyrimidine) (Cosmo Bio Co., Ltd., MedChemExpress) (PLoS One. 2012; 7 (9): e45845 (doi: 10.1371/journal.pone.004584.)), LDN-193189 (4-[6-(4-piperazin-1-yl-phenyl)-pyrazolo[1,5-α]pyrimidin-3-yl]-quinoline) and/or a hydrochloride thereof (MedChemExpress) (PLoS One. 2013 Apr. 30; 8 (4): e62721 (doi: 10.1371/journal.pone.0062721.)), 2-(3-(6-methylpyridin-2-yl)-1H-pyrazol-4-yl)-1,5-naphthyridine, K02288 (3-[6-amino-5-(3,4,5-trimethoxyphenyl)-3-pyridinyl]-phenol) (Tocris Bioscience) (PLoS One. 2013 Apr. 30; 8 (4): e62721 (doi: 10.1371/journal.pone.0062721.)), DMH-1 (4-[6-[4-(1-methylethoxy)phenyl]pyrazolo[1,5-α]pyrimidin-3-yl]-quinoline) (Cosmo Bio Co., Ltd., MedChemExpress) (ACS Chem Neurosci. 2012 Jun. 20; 3 (6): 482-91 (doi: 10.1021/cn300029t.)), LDN-212854 (5-(6-(4-(1-piperazinyl)phenyl)pyrazolo[1,5-α]pyrimidin-3-yl)quinoline) (Selleck Chemicals) (Bone. 2018 April; 109: 251-258 (doi: 10.1016/j.bone.2017.09.004.)), LDN-214117 (1-[4-[6-methyl-5-(3,4,5-trimethoxyphenyl)-3-pyridinyl]phenyl] piperazine) (J Med Chem. 2014 Oct. 9; 57 (19): 7900-15. (doi: 10.1021/jm501177w.)), and ML347 (5-[6-(4-methoxyphenyl)pyrazolo[1,5-a]pyrimidin-3-yl]quinoline) (Bioorg Med Chem Lett. 2013 Jun. 1; 23 (11): 3248-52. (doi: 10.1016/j.bmcl.2013.03.113.)). Alternatively, examples of the low-molecular weight compound that can be used as the BMPR signal transduction inhibitor of the present invention include compounds disclosed in International Publication No. WO2015/103355, International Publication No. WO2012/065059, International Publication No. WO2018/124001, International Publication No. WO2016/011019, International Publication No. WO2010/114860, International Publication No. WO2015/148654, International Publication No. WO2011/116212, International Publication No. WO2014/160203 and International Publication No. WO2016/054406.

The BMPR signal transduction inhibitor is preferably Type-I receptor signal transduction inhibitor. The BMPR signal transduction inhibitor is, a substance that can inhibit BMPR signal transduction, which is caused by binding of BMP including BMP4 to the receptor as a ligand. The BMPR signal transduction inhibitor is more preferably an ALK3 signal transduction inhibitor.

"ALK3 Signal Transduction Inhibitor"

ALK3 (Activin Receptor-Like Kinase 3) is also called as BMP receptor 1A (BMPR1A). ALK3 (BMPR1A), which is a Type-I receptor belonging to the BMP family, forms a hetero-tetramer with BMPR1B (the same Type-I receptor) and BMPR2 (Type II receptor) and then binds to a ligand to enable signal transduction into a cell.

The ALK3 signal transduction inhibitor according to the present invention acts anywhere in the signal transduction pathway from ALK3 and inhibits signal transduction mediated by an ALK3 ligand and ALK3. Examples of the ALK3 signal transduction inhibitor of the present invention include substances that inhibit the function of ALK3 (more specifically ALK3 inhibitor) by blocking or inhibiting the interaction between a ligand and ALK3 or by suppressing expression of ALK3 or a ligand thereof. Examples of the ALK3 ligand include BMP4, BMP2, BMP6 and BMP7, and a preferable ligand is BMP4.

Examples of the low-molecular weight compound that can be used as the ALK3 signal transduction inhibitor of the present invention include Dorsomorphin (6-[4-(2-piperidin-1-ylethoxy)phenyl]-3-pyridin-4-ylpyrazolo[1,5-a]pyrimidine) (Cosmo Bio Co., Ltd., MedChemExpress) (PLoS One. 2012; 7 (9): e45845 (doi: 10.1371/journal.pone.004584.)), LDN-193189 (4-[6-(4-piperazin-1-yl-phenyl)-pyrazolo[1,5-α]pyrimidin-3-yl]-quinoline) and/or a hydrochloride thereof (MedChemExpress) (PLoS One. 2013 Apr. 30; 8 (4): e62721 (doi: 10.1371/journal.pone.0062721.)), K02288 (3-[6-amino-5-(3,4,5-trimethoxyphenyl)-3-pyridinyl]-phenol) (Tocris Bioscience) (PLoS One. 2013 Apr. 30; 8 (4): e62721 (doi: 10.1371/journal.pone.0062721.)), DMH-1 (4-[6-[4-(1-methylethoxy)phenyl]pyrazolo[1,5-α]pyrimidin-3-yl]-quinoline) (Cosmo Bio Co., Ltd., MedChemExpress) (ACS Chem Neurosci. 2012 Jun. 20; 3 (6): 482-91 (doi: 10.1021/cn300029t.)), LDN-212854 (5-(6-(4-(1-piperazinyl)phenyl)pyrazolo[1,5-α]pyrimidin-3-yl)quinoline) (Selleck Chemicals) (Bone. 2018 April; 109: 251-258 (doi: 10.1016/j.bone.2017.09.004.)), LDN-214117 (1-[4-[6-methyl-5-(3,4,5-trimethoxyphenyl)-3-pyridinyl]phenyl] piperazine) (J Med Chem. 2014 Oct. 9; 57 (19): 7900-15. (doi: 10.1021/jm501177w.)) and ML347 (5-[6-(4-methoxyphenyl)pyrazolo[1,5-a]pyrimidin-3-yl]quinoline) (Bioorg Med Chem Lett. 2013 Jun. 1; 23 (11): 3248-52. (doi: 10.1016/j.bmcl.2013.03.113.)). Alternatively, examples of the low-molecular weight compound that can be used as the ALK3 signal transduction inhibitor of the present invention include compounds disclosed in International Publication No. WO2015/103355, International Publication No. WO2012/065059, International Publication No. WO2018/124001, International Publication No. WO2016/011019, International Publication No. WO2010/114860, International Publication No. WO2015/148654, International Publication No. WO2011/116212, International Publication No. WO2014/160203 and International Publication No. WO2016/054406.

Examples of the ALK3 signal transduction inhibitor include antagonists of an ALK3 ligand (including antagonist antibodies (antibodies against an anti-ALK3 ligand)), ALK3 antagonists (including antagonist antibodies (anti-ALK3 antibodies)), dominant negative ALK3 ligands, dominant negative ALK3; antisense nucleic acids or siRNA to mRNA of ALK3 ligands or ALK3. It is preferable that the ALK3 signal transduction inhibitor specifically acts on ALK3 or an ALK3 ligand. For example, in the case of an anti-ALK3 antibody, it is preferable that the antibody has a reactivity specific to ALK3 and does not substantially have a cross reactivity to another member of the ALK family, for example, ALK4. In the cases of an antisense nucleic acid and siRNA, it is preferable that they act specifically on a nucleic acid encoding ALK3 or an ALK3 ligand and does not act on a nucleic acid encoding another member (kinase) of the ALK family.

"Antibody or Fragment Thereof"

In the present invention, the antibody to be used as a BMPR signal transduction inhibitor may be either a polyclonal antibody or a monoclonal antibody and preferably a monoclonal antibody. These antibodies can be produced by a method known in the art. An isotype of the antibody, which is not particularly limited, is preferably, IgG, IgM or IgA and particularly preferably IgG. The antibody is not particularly limited as long as it has at least a complementarity determining region (CDR) for specifically recognizing a target antigen and binding it. Not only a complete antibody molecule but also a fragment such as Fab, Fab' and F(ab')$_2$, a conjugate molecule prepared in a genetic engineering procedure, such as scFv, scFv-Fc, minibody and diabody; or derivatives of these modified with a molecule having a protein stabilizing effect such as polyethylene glycol (PEG), may be used. In the specification, it is defined that examples of the "antibody" include derivatives of an antibody, such as an antibody modified with PEG, and examples of the "fragment" of the antibody include a conjugate molecule such as scFv, scFv-Fc, minibody and diabody.

The antibodies mentioned above may be commercially available antibodies or may be produced in accordance with a customary method. In producing antibodies, to reduce heterogeneous antigenicity to humans, Chimeric antibodies, Humanized antibodies or complete human antibodies are preferable.

"Dominant Negative"

The term "dominant negative" protein to be used as a BMPR signal transduction inhibitor refers to a mutant of a normal protein, which more excellently functions than a normal protein and inhibits the function of the normal protein to inhibit BMP signal transduction.

The dominant negative protein can be prepared by introducing a mutation in the sequence of a normal protein by use of, e.g., a commercially available kit in accordance with a technology known in the art and comparing the effect of a mutant protein on BMPR signal transduction with that of the normal protein.

"Antisense Nucleic Acid"

The antisense nucleic acid (antisense nucleic acid of the present invention) to be used as a BMPR signal transduction inhibitor refers to a nucleic acid having a nucleotide sequence complementary or substantially complementary to that of mRNA of a molecule involved in BMPR signal transduction or a part thereof and having a function to suppress protein synthesis of the molecule by specifically binding to the target mRNA to form a stable double strand. The antisense nucleic acid may be any one of double strand DNA, single strand DNA, double strand RNA, single strand RNA and a DNA/RNA hybrid.

The target region of an antisense nucleic acid is not particularly limited in length as long as the antisense nucleic acid is hybridized with the region, resulting in inhibition of translation of mRNA. The target region may be a whole or part sequence of the mRNA of a target molecule, and more specifically, the whole sequence of mRNA or an early transcript at the longest or a sequence having a length of about 10 nucleotides, at the shortest. In consideration of (easy) synthesis, antigenicity and intracellular migration, an oligonucleotide consisting of about 10 to 40 nucleotides, particularly about 15 to 30 nucleotides, is preferable but not limited to this. Examples of a preferable target region of an antisense nucleic acid that can be selected include, but are not limited to, a 5'-end hairpin loop, 5'-end 6 base-pair repeat, a 5'-end untranslated region, a translation initiation codon, a region encoding a protein, an ORF translation termination codon, a 3'-end untranslated region, 3'-end palindrome region or 3'-end hairpin loop of a target gene.

The nucleotide molecule constituting an antisense nucleic acid may be a natural nucleic acid, however, it may include various chemical modifications in order to improve the stability (chemical stability and/or stability to enzymes) and a specific activity (affinity with RNA). The antisense nucleic acid may be present in the form of an antigene. The antisense nucleic acids containing such various modifications can be synthesized by a method known in the art.

"SiRNA (Small Interfering RNA)"

SiRNA is double strand RNA consisting of an oligo-RNA strand, which is complementary to mRNA of a target molecule, and a complementary strand thereof, and can be synthesized based on the nucleotide sequence information of mRNA of a target molecule in accordance with a method known in the art. More specifically, siRNA is prepared by separately synthesizing a sense strand and antisense strand of a target sequence of mRNA, by a DNA/RNA automatic synthesizer, denaturing them in an appropriate annealing buffer at about 90 to 95° C. for about one minute, and then, annealing them at about 30 to 70° C. for about 1 to 8 hours. Alternatively, siRNA is prepared by synthesizing a siRNA precursor, i.e., short hairpin RNA (shRNA) and cutting the shRNA into pieces by a dicer The ribonucleotide molecule constituting siRNA may be chemically modified to improve, e.g., stability and specific activity as long as the molecule does not lose RNAi activity.

In the specification, a nucleic acid designed so as to generate the siRNA is also included in siRNA. Examples of the nucleic acid include shRNA and an expression vector constructed so as to express shRNA. ShRNA can be prepared by designing RNA (oligomer) having a nucleotide sequence, which was obtained by ligating a sense strand and an antisense strand of a target sequence of mRNA with a spacer sequence which is long sufficient to form an appropriate loop structure (for example, about 15 to 25 nucleotides), interposed between them, and synthesizing the RNA (oligomer) by a DNA/RNA automatic synthesizer. An expression vector having a shRNA expression cassette can be prepared by preparing a double strand DNA encoding the shRNA mentioned above and inserting the double strand DNA into an appropriate expression vector.

2. Suppression of Retinal Ganglion Cell Death

The present invention provides a retinal ganglion cell death suppressor comprising a BMPR signal transduction inhibitor. The present invention also provides a method for suppressing retinal ganglion cell death, comprising the steps of (a) administering an effective amount of a BMPR signal transduction inhibitor to a subject in need of the suppression; or (b) culturing retinal ganglion cells in the presence of an effective amount of a BMPR signal transduction inhibitor. Alternatively, the present invention provides a BMPR signal transduction inhibitor for use in suppression of retinal ganglion cell death.

Retinal ganglion cells (RGC) are nerve cells, which are present on the inner surface of the retina, convert visual information received from the photoreceptor cells into electric signals and transmit them to the brain. Since the retinal ganglion cells do not regenerate, it is important to elucidate mechanism of retinal ganglion cell death for preventing or treating various eye diseases including glaucoma.

The retinal ganglion cell death suppressor according to an embodiment of the invention refers to an agent containing a BMPR signal transduction inhibitor as an active ingredient, for suppressing cell death (apoptosis or necrosis, preferably apoptosis) of retinal ganglion cells by inhibiting signal transduction from BMPR. In the specification, the suppression of retinal ganglion cell death includes terminating or delaying progress of retinal ganglion cell death. More specifically, the suppression of retinal ganglion cell death means that the survival rate of the retinal ganglion cells is high in the presence of a BMPR signal transduction inhibitor compared to that in the absence of a BMPR signal transduction inhibitor. The survival rate of the cells can be analyzed by a method known in the art, more specifically, a method described in Examples. The BMPR signal transduction inhibitor is preferably a Type-I receptor signal transduction inhibitor, and more preferably, an ALK3 signal transduction inhibitor.

The retinal ganglion cell death suppressor according to the present invention may contain a pharmacologically acceptable carrier in addition to a BMPR signal transduction inhibitor. As the pharmacologically acceptable carrier, various types of organic or inorganic carriers routinely employed as pharmaceutical materials are mentioned. Examples of the pharmaceutical materials include materials for solid preparations such as an excipient, a lubricant, a binder and a disintegrant, and materials for liquid preparations such as a solvent, a solubilizing agent, a suspension agent, an isotonizing agent, a buffer agent and a soothing agent. If necessary, additives that are conventionally used, such as a preservative, an antioxidant, a colorant, a sweetener, an adsorbent and a wetting agent, can be used.

Examples of the excipient include lactose, white sugar, D-mannitol, starch, cornstarch, crystalline cellulose and light anhydrous silicic acid. Examples of the lubricant include magnesium stearate, calcium stearate, talc and colloidal silica. Examples of the binder include crystalline cellulose, white sugar, D-mannitol, dextrin, hydroxypropylcellulose, hydroxypropyl methylcellulose, polyvinylpyrrolidone, starch, sucrose, gelatin, methylcellulose and sodium carboxymethylcellulose. Examples of the disintegrant include starch, carboxymethylcellulose, calcium carboxymethylcellulose, sodium carboxymethyl starch and L-hydroxypropylcellulose. Examples of the solvent include water for injection, an alcohol, propylene glycol, macrogol, sesame oil, corn oil and olive oil. Examples of the solubilizing agent include polyethylene glycol, propylene glycol, D-mannitol, benzyl benzoate, ethanol, tris aminomethane, cholesterol, triethanolamine, sodium carbonate and sodium citrate. Examples of the suspension agent include a surfactant such as stearyl triethanolamine, sodium lauryl sulfate, laurylaminopropionic acid, lecithin, benzalkonium chloride, benzethonium chloride and glyceryl monostearate; and a hydrophilic polymer such as polyvinyl alcohol, polyvinylpyrrolidone, sodium carboxymethylcellulose, methylcellulose, hydroxymethylcellulose, hydroxyethylcellulose and hydroxypropylcellulose. Examples of the isotonizing agent include glucose, D-sorbitol, sodium chloride, glycerin and D-mannitol. Examples of the buffer agent include buffer solutions of a phosphate, an acetate, a carbonate and a citrate. Examples of the soothing agent include benzyl alcohol. Examples of the preservative include para-hydroxybenzoate, chlorobutanol, benzyl alcohol, phenethyl alcohol, dehydro acetic acid and sorbic acid. Examples of the antioxidant include a sulfite, ascorbic acid and α-tocopherol. Examples of the colorant include a water-soluble food tar dye (food dye such as food red No. 2 and No. 3, food yellow No. 4 and No. 5 and food blue No. 1 and No. 2), a water-insoluble lake pigment (e.g., aluminum salts of the water-soluble food tar dyes mentioned above), and a natural pigment (e.g., β-carotene, chlorophyll, bengara). Examples of the sweetener include sodium saccharin, dipotassium glycyrrhizinate, aspartame and stevia.

As the pharmacologically acceptable carrier, additives used in eye drops or eye ointments can be used, which include a stabilizer, a solubilizing agent, a suspension agent, an emulsifier, an isotonizing agent, a buffer agent, a thickening agent, a preservative, a pH regulator, a cooling agent and an ointment base.

Examples of the stabilizer include, sodium hydrogen sulfite, sodium thiosulfate, sodium edetate, sodium citrate, ascorbic acid and dibutylhydroxytoluene. Examples of the solubilizing agent include glycerin, propylene glycol, macrogol and polyoxyethylene hydrogenated castor oil. Examples of the suspension agent include polyvinylpyrrolidone, hydroxypropylmethylcellulose, hydroxymethylcellulose and sodium carboxymethylcellulose. Examples of the emulsifier include polyvinylpyrrolidone, soy lecithin, egg-yolk lecithin, polyoxyethylene hydrogenated castor oil and polysorbate 80. Examples of the isotonizing agent include sodium chloride, potassium chloride, glycerin, mannitol, sorbitol, boric acid, glucose and propylene glycol. Examples of the buffer agent include a phosphate buffer, an acetate buffer, a borate buffer, a carbonate buffer, a citrate buffer, a tris buffer, glutamic acid and epsilon aminocaproic acid. Examples of the thickening agent include water-soluble cellulose derivatives such as methylcellulose, hydroxyethylcellulose, hydroxypropyl methylcellulose and carboxymethylcellulose, sodium chondroitin sulfate, sodium hyaluronate, a carboxyvinyl polymer, a polyvinyl alcohol, polyvinylpyrrolidone and macrogol. Examples of the preservative include benzalkonium chloride, benzethonium chloride, chlorhexidine gluconate, chlorobutanol, benzyl alcohol, sodium dehydroacetate, paraoxybenzoate, sodium edetate and boric acid. Examples of the pH regulator include hydrochloric acid, sodium hydroxide, phosphoric acid and acetic acid. Examples of the cooling agent include l-menthol, d-camphor, d-borneol and peppermint oil. Examples of the ointment base include white petrolatum, purified lanolin, liquid paraffin, and vegetable oil (e.g., olive oil, camelia oil, peanut oil).

The retinal ganglion cell death suppressor according to the present invention can be prepared in accordance with a method known in the art by using a BMPR signal transduction inhibitor alone or in the mixture with a pharmacologically acceptable carrier. Examples of the preparation include eye drops, eye ointments, injections (for example, intravitreal injection, subconjunctival injection, sub-Tenon's injection, subcutaneous injection, intravenous injection, intramuscular injection, intraperitoneal injection), liquids, emulsions, suspensions, tablets (sugar-coated tablet, film-coated tablet, sublingual tablet, orally disintegrating tablet, buccal tablet), pills, powders, granules, capsules, lozenges, syrups, controlled-release preparations, aerosol agents, film agents, drops, transdermal absorption type pharmaceutical preparations, ointments, lotions, patches, suppositories (for example, anal suppository, vaginal suppository), pellets, transnasal agents and transpulmonary agents (inhalant). The retinal ganglion cell death suppressor can be safely administered, as a preparation as mentioned above, to mammals (preferably, human), orally or parenterally (for example, intravenous, intramuscular, subcutaneous, intraorgan, intranasal, intradermal, ocular topical administrations (e.g., eye drop administration, intravitreal administration, subconjunctival administration, sub-Tenon's administration), intrabrain, intrarectal, intravaginal, intraperitoneal, and diseased sites).

Eye drops can be prepared by using, if necessary, e.g., an isotonizing agent such as sodium chloride and concentrated glycerin; a buffering agent such as sodium phosphate and sodium acetate; a surfactant such as polyoxyethylene sorbitan monooleate, polyoxyl stearate 40, and polyoxyethylene hydrogenated castor oil; a stabilizer such as sodium citrate and sodium edetate; and a preservative such as benzalkonium chloride and paraben. A preferable solvent to be used for eye drops is purified water.

Eye ointments can be prepared by using, e.g., a base commonly used, such as white Vaseline and liquid paraffin. Oral preparations such as tablets, capsules, granules, fine granules and powders, can be prepared by adding, if necessary, e.g., a extender such as lactose, crystalline cellulose, starch and vegetable oil; a lubricant such as magnesium stearate and talc; a binder such as hydroxypropylcellulose and polyvinylpyrrolidone; a disintegrant such as calcium carboxymethylcellulose and low-substituted hydroxypropyl methylcellulose; a coating agent such as hydroxypropyl methylcellulose, macrogol and a silicone resin; and a coating material such as a gelatin film.

When an oral preparation is prepared, if necessary, coating may be applied for the purpose of masking of taste, enteric absorption or sustained release. Examples of the coating base include a sugar coating base, a water-soluble film coating base, an enteric film coating base and a sustained release film coating base.

As the sugar coating base, white sugar is used; and further, any one or more selected from, e.g., talc, precipitated calcium carbonate, gelatin, gum Arabic, pullulan and carnauba wax may be used alone or in combination. Examples of the water-soluble film coating base include cellulose polymers such as hydroxypropylcellulose, hydroxypropyl methylcellulose, hydroxyethylcellulose and methyl hydroxyethylcellulose; synthetic polymers such as polyvinyl acetal diethylaminoacetate, aminoalkyl methacrylate copolymer E [EUDRAGIT E (product name)] and polyvinylpyrrolidone; and polysaccharides such as pullulan. Examples of the enteric film coating base include cellulose polymers such as, hydroxypropylmethylcellulose phthalate, hydroxypropylmethylcellulose acetate succinate, carboxymethyl ethylcellulose and cellulose acetate phthalate; acrylic acid-based polymer such as methacrylate copolymer L, methacrylate copolymer LD and methacrylate copolymer S; and natural products such as shellac. Examples of the sustained release film coating base include cellulose polymers such as ethylcellulose; and acrylic acid-based polymers such as aminoalkyl methacrylate copolymer RS and ethyl acrylate-methyl methacrylate copolymer suspension. Two or more coating bases may be appropriately mixed and put in use. In coating, for example, a light-shielding agent such as titanium oxide and iron sesquioxide may be blended.

The administration route of the retinal ganglion cell death suppressor according to the present invention to a subject, which is not particularly limited, parenteral administration is preferable, more specifically, e.g., administration to a local part of an eye, injection administration, intranasal administration, transpulmonary administration, transdermal administration and transmucosal administration may be mentioned. Examples of the dosage form for administration to a local part of an eye include an eye drop and an eye ointment. Examples of injection administration include intravitreal injection, subconjunctival injection, sub-Tenon's injection, intravenous injection, intramuscular injection, intraperitoneal injection and subcutaneous injection. The method for administering the inhibitor can be appropriately selected depending on the age and symptom of a subject (for example, patient).

The dosage of the retinal ganglion cell death suppressor according to the present invention is not limited as long as BMPR signal transduction inhibitor as an active ingredient can be administered in an effective amount. The effective dosage of the BMPR signal transduction inhibitor, which is determined depending on, e.g., the purpose of use and the route of administration, is adjusted so as to obtain a desired favorable response (for example, response to therapy). In the present invention, the dosage of the active ingredient cannot be generally determined since the dosage varies depending on the target disease and the administration route; however, the dosage can be determined such that the concentration of the active ingredient in the target tissue, i.e., the retina tissue, in which the effect of the active ingredient is to be produced, falls in the range of 0.01 µM to 1000 µM, preferably 0.1 µM to 100 µM, and more preferably 1 µM to 10 µM. For example, in the case where an active ingredient is administered to a subject by ocular instillation, a medicinal agent containing the active ingredient in a concentration of 0.001 to 20 w/v %, preferably 0.1 to 10 w/v % and more preferably 1 to 5 w/v %, may be administered in a dose of about 20 to 50 µL per time, 1 to 8 times per day and preferably 1 to 5 times per day. For example, in the case where an active ingredient is intravitreally administered to a subject, the active ingredient may be administered in a dose of 0.01 ng to 100 mg, preferably 0.01 ng to 50 mg, more preferably 0.1 ng to 10 mg, and still further preferably 1 µg to 30 µg, once at the interval of 7 days to 2 months. In the case where an active ingredient is orally administered to a subject, the active ingredient may be administered in a dose of 10 ng to 1000 mg, preferably 100 ng to 500 mg, and more preferably 1 mg to 200 mg per time, 1 to 6 times and preferably 1 to 3 times per day.

Examples of the subject include mammals (for example, human, mouse, rat, hamster, rabbit, cat, dog, cow, sheep, monkey), preferably primates and more preferably humans.

According to an embodiment, retinal ganglion cell death is suppressed by administering an effective amount of a BMPR signal transduction inhibitor to a subject in need of suppression of retinal ganglion cell death. The administration route, dosage and others of the BMPR signal transduction inhibitor are the same as those described with respect to the retinal ganglion cell death suppressor. The BMPR signal transduction inhibitor may be formulated into a preparation with a pharmacologically acceptable carrier and administered. The pharmacologically acceptable carrier and preparation are the same as those described with respect to the retinal ganglion cell death suppressor.

According to an embodiment, retinal ganglion cell death can be suppressed by a step of culturing retinal ganglion cells in the presence of an effective amount of a BMPR signal transduction inhibitor. The retinal ganglion cells may be isolated from a living body or cultured cells. The retinal ganglion cells may be a group of cells or tissue containing retinal ganglion cells. Examples of the group of cells or tissue include retinal cells, neural retina cells, retinal neurons and retina tissue.

In a step of culturing retinal ganglion cells, a BMPR signal transduction inhibitor may be present in an effective amount in a culture liquid. The BMPR signal transduction inhibitor may be added to a culture solution in a concentration of 0.01 µM to 1000 µM, preferably 0.1 µM to 100 µM, and more preferably 1 µM to 10 µM.

3. Protection of Retinal Neurons

The retinal ganglion cell death suppressor according to the present invention can be used as a retinal neuroprotective agent for suppressing retinal ganglion cell death. Accordingly, the present invention provides a retinal neuroprotective agent comprising a BMPR signal transduction inhibitor. The present invention further provides a method for protecting retinal neurons, comprising the steps of (a) administering an effective amount of a BMPR signal transduction inhibitor to a subject in need of the retinal neuroprotection; or (b) culturing retinal neurons in the presence of an effective amount of a BMPR signal transduction inhibitor. Alternatively, the present invention provides a BMPR signal transduction inhibitor for use in protection of retinal neurons.

The retinal neuroprotective agent contains a BMPR signal transduction inhibitor as an active ingredient and exerts a retinal neuroprotective effect by inhibiting signal transduction from BMPR. Since 1,200,000 to 1,500,000 ganglion cells and about one-hundred million of photoreceptor cells are present in the human retina, a single ganglion cell receives information from thousands of photoreceptor cells, converts the information into electric signals and transmit them to the brain. The degeneration and cell death of the retinal ganglion cells lead to vision loss; however, there is no established treatment for these at present. The neuroprotective agent of the present invention protects the neural retina cells (particularly suppresses cell death of the retinal ganglion cells) involved in transmission of electric signals to the brain, through different mechanism of action from conventional neuroprotective agents and produces a neuroprotective effect. Owing to this, the neuroprotective agent can be expected to be applied to eye diseases which have been difficult to be treated. Moreover, the neuroprotective agent can be expected to have a prominent effect on eye diseases which have been treated by conventional treatment methods. In the specification, the retinal neuroprotection refers to not only suppressing neutral retina cell death induced by an unknown cause and/or functional deterioration of neural retina cells but also preventing neutral retina cell death that will occur in future and/or functional deterioration of neural retina cells.

The retinal neuroprotective agent of the present invention may contain a pharmacologically acceptable carrier in addition to a BMPR signal transduction inhibitor. Examples of the pharmacologically acceptable carrier are the same as those described with respect to the retinal ganglion cell death suppressor.

The neuroprotective agent of the present invention can be prepared in accordance with a method known in the art by using a BMPR signal transduction inhibitor alone or in the mixture with a pharmacologically acceptable carrier. Examples of the pharmacologically acceptable carrier, preparation, type of preparation, administration route and dosage are the same as those described with respect to the retinal ganglion cell death suppressor.

According to an embodiment, retinal neurons are protected by administering an effective amount of a BMPR signal transduction inhibitor to a subject in need of neuroprotection of the retina. The administration route, dosage and others of the BMPR signal transduction inhibitor are the same as those described with respect to the retinal ganglion cell death suppressor. The BMPR signal transduction inhibitor may be formulated into a preparation with a pharmacologically acceptable carrier and administered. The pharmacologically acceptable carrier and preparation are the same as those described with respect to the retinal ganglion cell death suppressor.

According to an embodiment, retinal neurons can be protected by a step of culturing retinal neurons in the presence of an effective amount of a BMPR signal transduction inhibitor. As the retinal neurons, any retinal neurons are available as long as they contain retinal ganglion cells.

In a step of culturing retinal neurons, a BMPR signal transduction inhibitor may be present in an effective amount in a culture solution. The BMPR signal transduction inhibitor may be added to a culture solution in a concentration of 0.01 µM to 1000 µM, preferably 0.1 µM to 100 µM, and more preferably 1 µM to 10 µM.

4. Prevention or Treatment of Disease Involving Retinal Ganglion Cell Death

The retinal ganglion cell death suppressor and retinal neuroprotective agent according to the present invention can be used in a pharmaceutical composition for preventing or treating a disease involving retinal ganglion cell death. The present invention also provides a medicinal agent comprising a BMPR signal transduction inhibitor for preventing or treating a disease involving retinal ganglion cell death. The present invention further provides a method for preventing or treating a disease involving retinal ganglion cell death, comprising a step of administering an effective amount of a BMPR signal transduction inhibitor to a subject in need of the prevention or treatment. Alternatively, the present invention provides a BMPR signal transduction inhibitor for use in prevention or treatment of a disease involving retinal ganglion cell death.

A disease involving retinal ganglion cell death refers to a disease caused by cell death of retinal ganglion cells, and all diseases (particularly eye diseases) having pathological conditions of retinal ganglion cell death or damages of retinal ganglion cells. Examples of the disease include glaucoma, diabetic retinopathy, retinal vascular occlusion (including retinal artery occlusion or retinal vein occlusion), ischemic optic neuropathy, Leber disease, a disease associated with choroidal neovascularization, retinitis pigmentosa, dominant hereditary optic atrophy, optic neuritis and aniridia.

"Glaucoma"

Glaucoma is a progressive disease having characteristic changes in the optic nerve and the field of view, and conceivably caused by retinal ganglion cell death. As the cause of the retinal ganglion cell death, e.g., depletion of nutrients (ischemia) in cells due to elevation of intraocular pressure, and oxidative stress, are mentioned. Accordingly, protecting the retinal ganglion cells is useful for treatment for glaucoma (Liu et al., Invest Ophthalmol Vis Sci. 2017 Oct. 1; 58 (12): 5129-5141).

"Diabetic Retinopathy"

Diabetic retinopathy is retinopathy that occurs as diabetes complication. The blood vessels of the retina are damaged and degenerated by continuous hyperglycemic condition due to diabetes, with the result that ischemia and oxygen deficiency of the retina occur. In diabetic retinopathy, it is known that adverse factors such as hypoxia, excitotoxicity and oxidative stress-induced retinal ganglion cell death are involved in onset thereof (Xiao A et al., Exp Ther Med. 2017 June; 13 (6): 3360-3368).

"Ischemic Optic Neuropathy"

Ischemic optic neuropathy is a disease having impaired circulation in blood vessels providing nutrition to the optic nerve. Retinal ganglion cell death induced by retinal ischemia due to oxidative stress is a pathology commonly observed in ischemic optic neuropathy (Kapupara K et al., Cell death Dis. 2017 Nov. 16; 8 (11)).

"Retinal Vascular Occlusion"

Retinal vascular occlusion is a disease caused by blood clotting in the retina and thereby blood flow to cells is stopped. Retinal artery occlusion and retinal vein occlusion are included. Blockage (ischemia) of blood flow causes depletion of nutrients and lack of oxygen in the retinal cells, resulting in cell death. In retinal vascular (artery or vein) occlusion, retinal ganglion cell death caused by retinal ischemia due to oxidative stress is a pathology commonly observed (Kapupara K et al. mentioned above).

"Leber Disease"

Leber disease (Leber's hereditary optic neuropathy) is a hereditary optic neuropathy, which is a disease caused by abnormality in a gene of mitochondria responsible for energy production. It is considered that apoptosis of retinal ganglion cells is caused by genetic mutation, and presumed that oxidative stress is involved in the onset of the disease (Guy J, et al., Invest Ophthalmol Vis Sci. 2014 Feb. 10; 55 (2): 841-8).

"Dominant Hereditary Optic Atrophy"

Dominant hereditary optic atrophy is a hereditary optic neuropathy, similarly to Leber disease. The atrophy is autosomal dominantly inherited and has degeneration of retinal ganglion cells as a pathological condition. This disease is conceivably associated with OPA1 genetic mutation, and reported that prevention of retinal ganglion cell loss by OPA1 gene transfer can be a treatment means (Sarzi E, et al., Sci Rep. 2018 Feb. 6; 8 (1): 2468).

"Optic Neuritis"

Optic neuritis is a disease having low vision and vision disturbance caused by inflammation in the optic nerve and optic nerve loss including apoptosis of retinal ganglion cells occurs (Khan R S, Invest Ophthalmol Vis Sci. 2014 Aug. 19; 55 (9): 5744-51).

"Aniridia"

Aniridia is a state where iris is congenitally not formed and caused by abnormality in PAX6 gene. Since aniridia sometimes occurs in combination with glaucoma, an optic nerve disorder including apoptosis of retinal ganglion cells occurs (W M Grant and D S Walton, Trans Am Ophthalmol Soc. 1974; 72: 207-228.)

"Retinitis Pigmentosa"

The retina is a tissue sensitive to light. When light strikes the retina, an electrical signal is generated and transmitted to the brain through the optic nerve. Retinitis pigmentosa is a hereditary disease having abnormality in the retina, and night blind, tunnel vision and low vision are known as characteristic symptoms. A retinal neuroprotective agent is considered to delay progress of retinitis pigmentosa and development of the agent is expected.

"Disease Associated with Choroidal Neovascularization"

Choroidal neovascularization refers to ectopic proliferation of choroid blood vessels and bleeding from immature vascular network and leakage of plasma components containing fat are known to rapidly impair the function of the retinal neurons. Examples of the disease having choroidal neovascularization include myopic choroidal neovascularization, idiopathic choroidal neovascularization, posterior eye uveitis, traumatic choroid rupture and angioid streaks of retina. Myopic choroidal neovascularization is a disease most frequently observed in persons having pathological myopia and causing deterioration of vision.

5. Pharmaceutical Composition for Preventing or Treating Disease Involving Retinal Ganglion Cell Death A pharmaceutical composition for preventing or treating a disease involving retinal ganglion cell death (hereinafter referred to as "the pharmaceutical composition of the present invention") contains a BMPR signal transduction inhibitor as an active ingredient, similarly to a retinal ganglion cell death suppressor, and prevents or treats a disease involving retinal ganglion cell death by inhibiting BMPR signal transduction. The BMPR signal transduction inhibitor is preferably a Type-I receptor signal transduction inhibitor, and more preferably, an ALK3 signal transduction inhibitor.

The pharmaceutical composition of the present invention may contain a pharmacologically acceptable carrier in addition to BMPR signal transduction inhibitor. Examples of the pharmacologically acceptable carrier are the same as those described with respect to the retinal ganglion cell death suppressor.

The pharmaceutical composition of the present invention can be prepared in accordance with a method known in the art by using a BMPR signal transduction inhibitor alone or in the mixture with a pharmacologically acceptable carrier. Examples of the preparation, pharmacologically acceptable carrier, type of preparation, administration route and dosage are the same as those described with respect to the retinal ganglion cell death suppressor.

The pharmaceutical composition according to the present invention can be used in combination with another medical drug. Examples of the medical drug that can be used in combination (hereinafter referred to simply as concomitant drug) include an anti-glaucoma drug, an anti-obesity agent, a therapeutic agent for diabetes, a therapeutic agent for a diabetic complication, an antihypertensive, a diuretic agent, a therapeutic agent for hyperlipidemia, a chemotherapeutic agent, an immunotherapeutic agent, an anti-inflammatory drug, an antithrombotic agent, a therapeutic agent for osteoporosis, a vitamin preparation, a therapeutic agent for dementia, a therapeutic drug for frequent urination or urinary incontinence and a therapeutic drug for dysuria.

According to an embodiment, a disease involving retinal ganglion cell death is prevented or treated by administering an effective amount of a BMPR signal transduction inhibitor to a subject in need of prevention or treatment of a disease involving retinal ganglion cell death. The administration route and dosage of a BMPR signal transduction inhibitor are the same as those described with respect to the retinal ganglion cell death suppressor. The BMPR signal transduction inhibitor may be formulated into a preparation with a pharmacologically acceptable carrier and administered. The pharmacologically acceptable carrier, and preparation are the same as those described with respect to the retinal ganglion cell death suppressor.

6. Use for Regenerative Medicine

Recently in the treatment for eye diseases, regenerative medicine has attracted attention. For example, a treatment for eye diseases with a material for regenerative medicine produced from optic nerve or retinal ganglion cells has been investigated. The retinal ganglion cell death suppressor according to the present invention can be used as a retinal cell transplantation adjuvant or a regenerative medicine adjuvant in producing and storing a material for regenerative medicine and in the treatment using the material. More specifically, the retinal ganglion cell death suppressor according to the present invention can be used by adding it in a culture medium in a step of producing a material for regenerative medicine such as a cell preparation or cell sheet or a step of storing the material for regenerative medicine before transplantation. The present invention provides a method for culturing retinal cells by adding a retinal cell transplantation adjuvant or regenerative medicine adjuvant comprising the retinal ganglion cell death suppressor or retinal neuroprotective agent according to the present invention, and culturing retinal cells.

The above retinal cell transplantation adjuvant or regenerative medicine adjuvant of the present invention may be contained in a cell preparation. The present invention encompasses the cell preparation. The cell preparation is satisfactory as long as it contains retinal ganglion cells such as retinal cells for transplantation. The cells may be a culture after culturing. Cell death of the retinal ganglion cells is suppressed by adding the retinal ganglion cell death suppressor according to the present invention and a tissue can be effectively regenerated. The retinal cell transplantation adjuvant or regenerative medicine adjuvant of the present invention may contain, if necessary, a substance for promoting or assisting adhesion to an affected site. Examples of the substance include cell-adhesion peptides such as an extracellular matrix including Matrigel™, collagen, fibronectin, vitronectin, RetroNectin, laminin, cadherin, integrin, selectin and RGD peptide. The cell preparation of the present invention can be processed into the dosage form of, for example, an injection and an impregnating agent, and locally administered in the retina.

The dosage form and shape of the above cell preparation of the present invention, which are not particularly limited, may be a cell sheet prepared by stratifying a plurality of retinal ganglion cell layers. As an embodiment of the cell sheet, for example, a cell sheet having a cell layer formed of retinal ganglion cells having extended axons and maintaining cell-cell interaction, is mentioned. Such a cell sheet (a culture of retinal ganglion cells) can be directly transplanted to affected sites as it is.

EXAMPLES

The present invention will be more specifically described below by way of Examples; however, the present invention is not limited to these Examples.

A culture system of retinal ganglion cells exposed to oxidative stress is considered as a cell damage model and commonly used for checking a neuroprotective effect. Menadione, a kind of vitamin K, is known to induce a cell damage model due to oxidative stress. Because of this, in the following Examples, a cell damage model was induced by menadione (Invest Ophthalmol Vis Sci. 2006 April; 47 (4): 1477-85, J Neurochem. 2010 July; 114 (2): 488-98 (doi: 10.1111/j.1471-4159.2010.06781.x.), J Ophthalmol. 2017; 2017: 7598140 (doi: 10.1155/2017/7598140)).

Example 1

In the Example, a neuroprotective effect was checked by specifically inhibiting BMPR (particularly ALK3) in retinal ganglion cells, thereby inhibiting signal transduction from BMPR (particularly ALK3). As a negative control, a case where ALK4 was specifically inhibited was used and the neuroprotective effect of the case was checked. ALK4 belongs to the same ALK family as ALK3, and controls not the BMPR signal transduction system but the signal transduction using activin as a ligand.

1. Method (1) Isolation of Rat Retinal Ganglion Cells

The retina was taken out from each of 7 days-old SD rats (13 rats) (Japan SLC Co., Ltd.) and retinal cells were dispersed by Dissociation Kit-Postnatal Neurons (Miltenyi Biotec). Thereafter, retinal ganglion cells (RGC) were isolated from other retinal cells by use of Retinal Ganglion Cell Isolation Kits (Miltenyi Biotec).

(2) Menadione, Antibody Treatment

The retinal ganglion cells were suspended in RGC culture medium, seeded in the wells of a 96-well plate at a density of $2 \times 10^4$ cells/well and cultured at 37° C. under a 5% $CO_2$ atmosphere for 24 hours. Twenty four hours later, the medium was removed. To a medium for a menadione reaction, 6 μM menadione, Normal rabbit IgG (Santa Cruz Biotechnology, Inc.), an anti-ALK3 antibody (Anti-BMPR1A antibody, Abcam plc.), an anti-ALK4 antibody (anti-Activin A receptor Type IB antibody, Abcam plc.) and an ALK3 inhibitor, i.e., K02288 (Tocris Bioscience) (PLOS ONE 2013 8 (4) e62721) were added in accordance with the constitutions of individual groups (described later) and incubation was performed at 37° C. for 18 hours. Thereafter, survival cells and dead cells were stained by use of LIVE/DEAD Viability/Cytotoxicity Kit (Thermo Fisher Scientific Inc.). Three photographs per well were taken by IncuCyte S3 live cell analysis system (Essen Bioscience) and analyzed. Data was calculated as the ratio of the number of survival cells relative to a total number of dead cells and survival cells. The RGC culture medium and medium used for a menadione reaction are as follows.

RGC Culture Medium:

A medium prepared by adding, to Neurobasal medium (Thermo Fisher Scientific Inc.), NeuroBrew-21 supplement (Miltenyi Biotec), 50 ng/mL BDNF (Miltenyi Biotec), 50 ng/mL CNTF (Peprotech, Inc.), 5 μM Forskolin (Sigma-Aldrich Co. LLC.), GlutaMAX™ (Thermo Fisher Scientific Inc.) and Primocin™ (InvivoGen.).

Medium for a Menadione Reaction:

A medium prepared by adding, to Neurobasal medium (Thermo Fisher Scientific Inc.), NeuroBrew-21 supplement (Miltenyi Biotec), GlutaMAX™ (Thermo Fisher Scientific Inc.) and Primocin™ (InvivoGen.).

Constitutions of Groups (Each Group n=3):

Control group: menadione was absent and Normal rabbit IgG was added;
A group treated with Normal IgG: menadione and Normal rabbit IgG were added;
A group treated with an anti-ALK3 antibody: menadione and an anti-ALK3 antibody were added;
A group treated with an anti-ALK4 antibody: menadione and an anti-ALK4 antibody were added;
A group treated with K02288: menadione and K02288 were added.

(3) Specificity of Antibody

The retina was taken out from a single 7 days-old SD rat (Japan SLC Co., Ltd.,) and a membrane fraction was extracted by use of Subcellular Protein Fractionation Kit (Thermo Fisher Scientific Inc.), and then, treated with PNGase F (New England BioLabs, Inc.) to cut a sugar chain. The samples obtained were subjected to western blot; more specifically, the samples were applied to SDS-PAGE so as to contain an equal amount of protein. The proteins separated by SDS-PAGE were transferred onto a PVDF membrane, and allowed to react with an anti-ALK3 antibody alone, an anti-ALK3 antibody+ALK3 (BMPR1A) peptide (Abnova Corporation.)(double amount of the anti-ALK3 antibody), an anti-ALK4 antibody alone, or anti-ALK4 antibody+ALK4 (ACVR1B) peptide (Abnova Corporation.)(double amount of anti-ALK4 antibody). The anti-ALK3 antibody and ALK3 peptide as well as the anti-ALK4 antibody and ALK4 peptide were mixed in advance and allowed to react at 37° C. for one hour. Each of the mixtures obtained after completion of the reaction was allowed to react with the PVDF membrane on which proteins were transferred; and thereafter, stained with a secondary antibody, i.e., an anti-rabbit HRP antibody (GE Health Care). The staining results were photographed by ImageQuant LAS4000 (GE Health Care).

2. Results

In the Normal IgG group, significant cell death was induced by the menadione treatment. In contrast, in the group treated with the anti-ALK3 antibody group and the group treated with an ALK inhibitor, i.e., K02288, cell death was significantly suppressed. In contrast, in the group treated with the anti-ALK4 antibody, i.e., an antibody to ALK4, which is the same TGF β super family receptor as ALK3 (FIG. 1C), cell death was not suppressed.

Note that, as shown in FIGS. 1A and 1B, in the cases where the anti-ALK3 antibody and the anti-ALK4 antibody were used alone, dark bands were obtained. In contrast, in the cases where the antibodies were used in combination with the corresponding peptides thereof, thin (light) bands were obtained. The anti-ALK3 antibody and anti-ALK4 antibody used herein reacted with ALK3 and ALK4 in the retina tissue, respectively, and reactions with ALK3 and ALK4 in the retina tissue are blocked by the ALK3 peptide, and the ALK4 peptide serving as antigens, respectively. Thus, it was confirmed that the anti-ALK3 antibody and anti-ALK4 antibody specifically bind to ALK3 and ALK4, respectively (FIGS. 1A and 1B).

The anti-ALK3 antibody used herein specifically reacts to ALK3. Accordingly, the cell death inhibitory effect by the anti-ALK3 antibody is considered to be specific to ALK3.

Example 2

In Example 1, it was confirmed that the neuroprotective effect on retinal ganglion cells is produced by inhibiting signal transduction from BMPR, particularly signal transduction from ALK3. In Example 2, the neuroprotective effect on retinal ganglion cells in the case where a low-molecular weight compound serving as an ALK3 inhibitor was used, was checked.

1. Method (1) Isolation of Rat Retinal Ganglion Cells

Rat retinal ganglion cells were isolated in the same manner as in Example 1. In the experimental system (FIG. 2A) of K02288 treatment, three rats were used; whereas, in the experimental system (FIG. 2B) of LDN-193189 treatment, two rats were used.

(2) Measurement of Retinal Ganglion Cell Death

Retinal ganglion cells were suspended in RGC culture medium and seeded in the wells of a 96-well plate at a density of $1\times10^4$ cells/well and cultured at 37° C. under a 5% $CO_2$ atmosphere for 24 hours. Twenty four hours later, the medium was removed. To a medium for a menadione reaction, 6 μM menadione and ALK3 inhibitors, i.e., K02288 (Tocris Bioscience) or LDN-193189 (MedChemExpress) (PLOS ONE 2013 8 (4) e62721) were added in accordance with the constitutions of individual groups. DMSO was added to a non K02288 treatment group or a non LDN-193189 treatment group, (a group treated with menadione alone). The cells were incubated at 37° C. for 18 hours and thereafter stained by use of LIVE/DEAD Viability/Cytotoxicity Kit (Thermo Fisher Scientific Inc.). Three photographs per well were taken by use of IncuCyte S3 live cell analysis system (Essen Bioscience) and analyzed. Data was calculated as the ratio of the number of survival cells relative to a total number of dead cells and survival cells. The RGC culture medium and medium for a menadione reaction used herein are the same as those used in Example 1.

Constitutions of groups (a group treated with K02288: n=8, a group treated with LDN-193189: n=6)

Control group: menadione was absent

A group treated with menadione alone: menadione and DMSO were added

A group treated with K02288 (3 groups: 100 nM, 1 μM, 10 μM): menadione and K02288 were added A group treated with LDN-193189 (2 groups: 100 nM, 1 μM): menadione and LDN-193189 were added.

2. Results

Figure 2B:
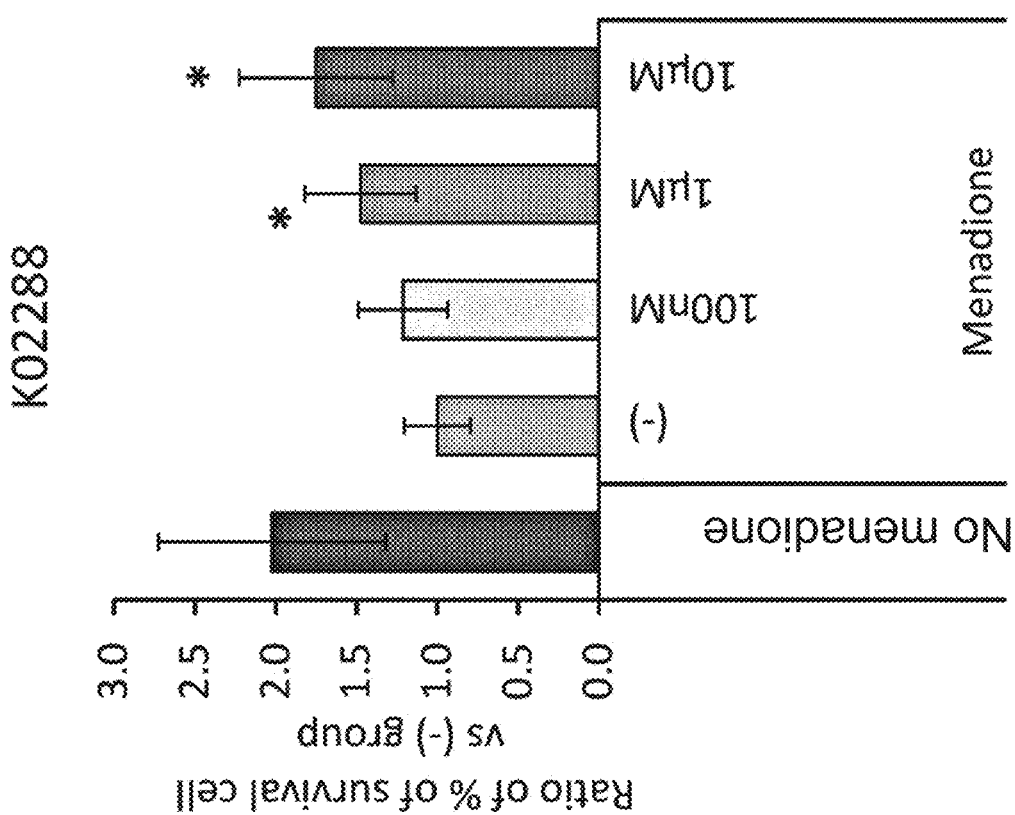
FIG. 2B shows the effect of a BMPR signal transduction inhibitor LDN-193189 on retinal ganglion cell death induced by menadione. The vertical axis represents the ratio (%) of the number of survival cells relative to that of a group treated with menadione alone; whereas, the horizontal axis represents test samples: Control group (menadione−), Group treated with menadione alone; Group treated with 100 nM LDN-193189; and Group treated with 1 μM LDN-193189, in this order from the left. *$P<0.05$ Dunnett's test vs a group treated with menadione alone, n=6.

The groups treated with 1 μM and 10 μM K02288 showed a significant cell death inhibitory effect compared to the group treated with menadione alone. The group treated with 1 μM LDN-193189 showed a significant cell death inhibitory effect compared to the group treated with menadione alone (FIGS. 2A and 2B). K02288 and LDN-193189 exhibited a cell death inhibitory effect in a dose-dependent manner. The BMPR inhibitors (K002288, LDN-193189) exerted an effect to protect cells from retinal ganglion cell death induced by menadione.

Example 3

The Example was carried out in order to confirm expression of BMPR ligand in retinal ganglion cells and in a cell damage model. Also, in the Example, expression of the receptor of the TGF β super family, to which a BMPR ligand in retinal ganglion cells is to be bound, was checked.

1. Method (1) Isolation of Rat Retinal Ganglion Cells

Rat retinal ganglion cells were isolated in the same manner as in Example 1. Note that, in an experimental system for confirming expression of a receptor of the TGF β super family, 10 rats were used. In an experimental system for confirming expression of a BMPR ligand, 30 rats were used.

(2) Menadione Treatment

The retinal ganglion cells were suspended in RGC culture medium, seeded in the wells of a 6-well plate at a density of $2.83\times10^5$ cells/well and cultured at 37° C. under a 5% $CO_2$ atmosphere for 24 hours. Twenty four hours later, the medium was removed, and a medium prepared by adding 6 μM menadione to a medium for a menadione reaction was replaced. The cells were incubated at 37° C. for 0 hour or 6 hours (n=2). After completion of the incubation, the medium was removed and the cells were lysed in a 1 mL Trizol reagent and subjected to RNA extraction. The RGC culture medium and medium for a menadione reaction were the same as described in Example 1.

(3) RNA Extraction

RNA was extracted by use of RNeasy Mini Kit (QIAGEN) in accordance with a manual. After completion of RNA extraction, cDNA was obtained by reverse transcription using Superscript II reverse transcriptase (Thermo Fisher Scientific Inc.).

(4) Real Time qPCR

To the cDNA, each of TaqMan probe and TaqMan Master Mix were mixed and qPCR analysis was carried out by use of 7500 PCR systems (Applied Biosystems). A calibration curve was prepared for each of the targets, the copy number was obtained and corrected based on the measured value of GAPDH to obtain an expression level. With respect to a ligand, the ratio of copy number after menadione treatment of 6 hours to the copy number of menadione treatment 0 hour was calculated. The same experiment was repeated twice and reproducibility was confirmed.

TaqMan probe (receptor): ALK4, Bmpr2, Acvr2a, Acvr2b, ALK2, ALK3, ALK6, ALK7

TaqMan probe (ligand): Inhba, Tgfb2, Tgfb1, Gdf5, Bmp7, Bmp4, Bmp2, Gapdh

2. Results

Figure 3:
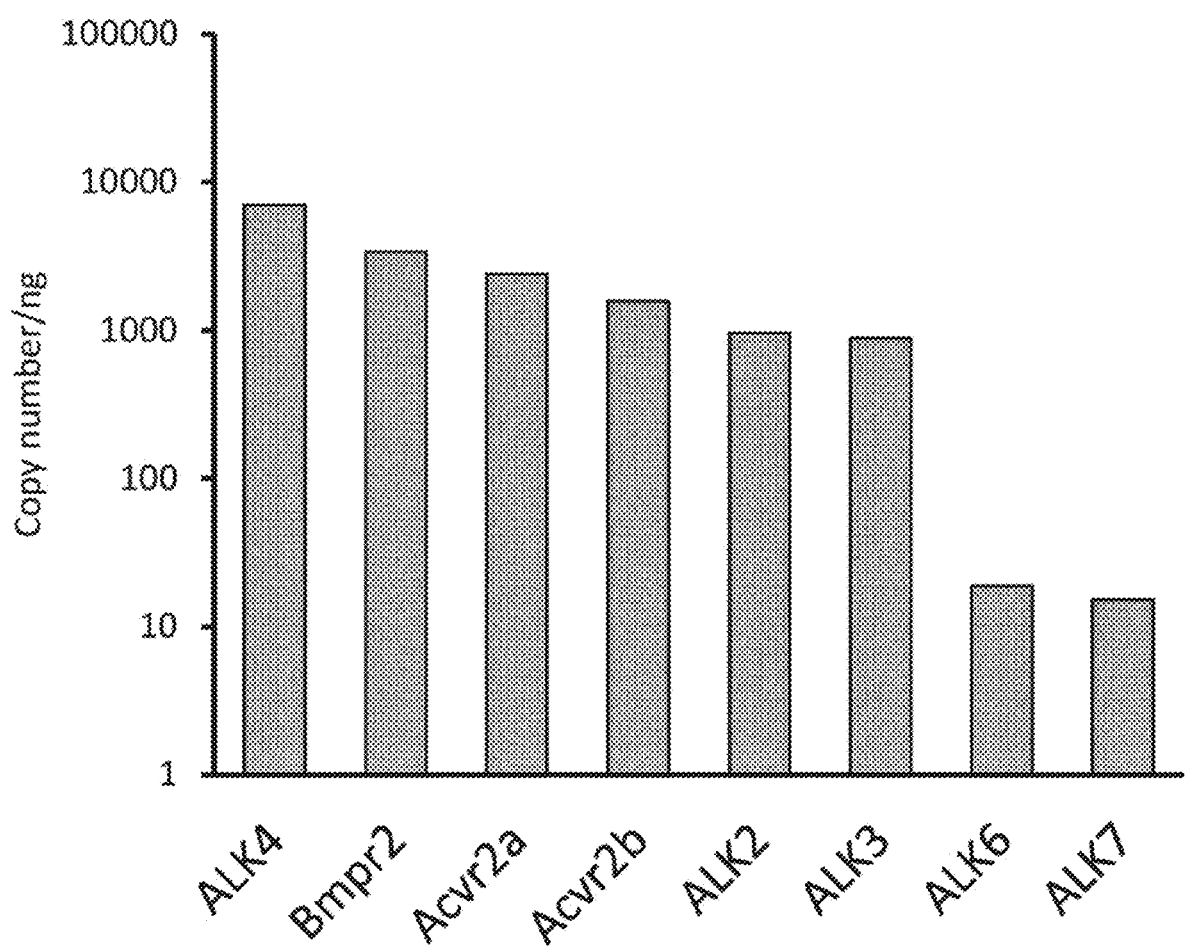
FIG. 3 shows the mRNA expression level of individual receptors of the TGF β super family in retinal ganglion cells. The vertical axis represents the copy number per RNA 1 ng; whereas, the horizontal axis represents the names of receptors: ALK4, Bmpr2, Acvr2a, Acvr2b, ALK2, ALK3, ALK6 and ALK7, in this order from the left.

In the retinal ganglion cells to which menadione was not added, the expressions of mRNAs of various receptors of TGF β super family were confirmed (FIG. 3).

Figure 4:
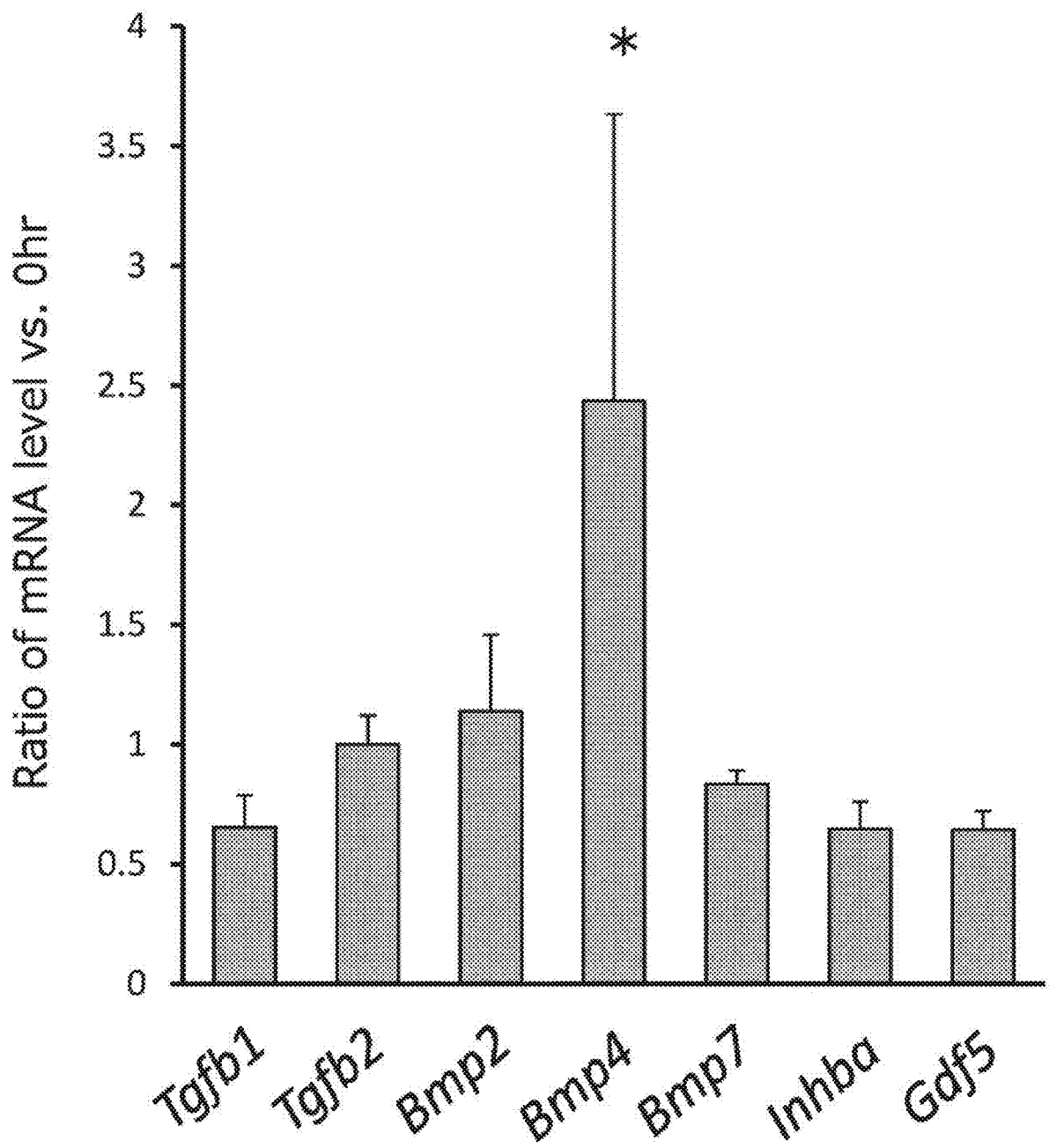
FIG. 4 shows the mRNA expression level of a BMP ligand in retinal ganglion cells treated with menadione. The vertical axis represents the ratio of the copy number of a sample treated with menadione for 6 hours relative to that of a sample not treated with menadione; whereas, the horizontal axis represents the names of ligands: Tgfb1, Tgfb2, Bmp2, Bmp4, Bmp7, Inhba and Gdf5, in this order from the left. n=2.

Six hours after addition of menadione, expression of BMP4 in the retinal ganglion cells increased at least to double (FIG. 4). Ligands of the TGF β super family except BMP4, i.e., TGFβ1, TGFβ2, BMP2, BMP7, InhibinβA and GDF5, were confirmed to be expressed in the retinal ganglion cells; however, it was confirmed that expression of particularly BMP4 remarkably increased in the presence of menadione. From the above results, it was considered that BMP4 is particularly involved in the cell death of retinal ganglion cells induced by menadione.

(Summary)

In the retinal ganglion cells placed under oxidative stress due to menadione, it was confirmed from Example 3 that the expression level of particularly BMP4 remarkably increases. Furthermore, based on Example 1, it was confirmed that cell death due to oxidative stress is suppressed by specifically inhibiting the function of ALK3 by an extracellular recognition antibody to ALK3. Moreover, based on Examples 1 and 2, induced cell death due to oxidative stress is suppressed also by an ALK3 inhibitor other than an antibody. From the above, it was confirmed that inhibition of signal transduction from BMPR, particularly ALK3 plays an important role in suppression of retinal ganglion cell death and will be a new target for development of retinal neuroprotective agents.

INDUSTRIAL APPLICABILITY

The BMPR signal transduction inhibitor of the present invention is useful for use in treatment of a disease involving retinal ganglion cell death, such as glaucoma, diabetic retinopathy and retinal vascular occlusion.

All publications, Patents and Patent applications cited in the specification are incorporated herein in their entirety by reference.

The invention claimed is:

1. A method for suppressing retinal ganglion cell death comprising culturing retinal ganglion cells in the presence of an effective amount of an Activin Receptor-like Kinase 3 (ALK3) signal transduction inhibitor, wherein the ALK3 signal transduction inhibitor is at least one selected from the group consisting of an anti-ALK3 antibody or a fragment thereof that binds ALK3, an anti-BMP4 antibody or a fragment thereof that binds BMP4, LDN-193189 (4-[6-(4-piperazin-1-yl-phenyl)-pyrazolo[1,5-α]pyrimidin-3-yl]-quinoline), 2-(3-(6-methylpyridin-2-yl)-1H-pyrazol-4-yl)-1,5-naphthyridine, K02288 (3-[6-amino-5-(3,4,5-trimethoxyphenyl)-3-pyridinyl]-phenol), DMH-1 (4-[6-[4-(1-methylethoxy)phenyl]pyrazolo[1,5-α]pyrimidin-3-yl]-quinoline), LDN-212854 (5-(6-(4-(1-piperazinyl)phenyl)pyrazolo[1,5-α]pyrimidin-3-yl)quinoline), LDN-214117 (1-[4-[6-methyl-5-(3,4,5-trimethoxyphenyl)-3-pyridinyl]phenyl] piperazine), ML347 (5-[6-(4-methoxyphenyl)pyrazolo[1,5-α]pyrimidin-3-yl]quinoline), an ALK3 antisense nucleic acid or siRNA, and a BMP4 antisense nucleic acid or siRNA, wherein the fragment is at least one selected from the group consisting of a Fab, a F(ab')2, a Fv, a scFv, a scFv-Fc, a minibody, and a diabody.

2. The method according to claim 1, wherein the retinal ganglion cells are cells for transplantation.

3. A method for protecting a retinal neuron comprising culturing the retinal neuron in the presence of an effective amount of an Activin Receptor-like Kinase 3 (ALK3) signal transduction inhibitor, wherein the ALK3 signal transduction inhibitor is at least one selected from the group consisting of an anti-ALK3 antibody or a fragment thereof that binds ALK3, an anti-BMP4 antibody or a fragment thereof that binds BMP4, LDN-193189 (4-[6-(4-piperazin-1-yl-phenyl)-pyrazolo[1,5-α]pyrimidin-3-yl]-quinoline), 2-(3-(6-methylpyridin-2-yl)-1H-pyrazol-4-yl)-1,5-naphthyridine, K02288 (3-[6-amino-5-(3,4,5-trimethoxyphenyl)-3-pyridinyl]-phenol), DMH-1 (4-[6-[4-(1-methylethoxy)phenyl] pyrazolo[1,5-α]pyrimidin-3-yl]-quinoline), LDN-212854 (5-(6-(4-(1-piperazinyl)phenyl)pyrazolo[1,5-α]pyrimidin-3-yl)quinoline), LDN-214117 (1-[4-[6-methyl-5-(3,4,5-trimethoxyphenyl)-3-pyridinyl]phenyl] piperazine), ML347 (5-[6-(4-methoxyphenyl)pyrazolo[1,5-α]pyrimidin-3-yl] quinoline), an ALK3 antisense nucleic acid or siRNA, and a BMP4 antisense nucleic acid or siRNA, wherein the fragment is at least one selected from the group consisting of a Fab, a F(ab')2, a Fv, a scFv, a scFv-Fc, a minibody, and a diabody.

4. A method for treating a disease involving retinal ganglion cell death comprising administering an effective amount of an Activin Receptor-like Kinase 3 (ALK3) signal transduction inhibitor to a subject in need of the treatment, wherein the ALK3 signal transduction inhibitor is at least one selected from the group consisting of an anti-ALK3 antibody or a fragment thereof that binds ALK3, an anti-BMP4 antibody or a fragment thereof that binds BMP4, LDN-193189 (4-[6-(4-piperazin-1-yl-phenyl)-pyrazolo[1,5-α]pyrimidin-3-yl]-quinoline), 2-(3-(6-methylpyridin-2-yl)-1H-pyrazol-4-yl)-1,5-naphthyridine, K02288 (3-[6-amino-5-(3,4,5-trimethoxyphenyl)-3-pyridinyl]-phenol), DMH-1 (4-[6-[4-(1-methylethoxy)phenyl]pyrazolo[1,5-α] pyrimidin-3-yl]-quinoline), LDN-212854 (5-(6-(4-(1-piperazinyl)phenyl)pyrazolo[1,5-α]pyrimidin-3-yl) quinoline), LDN-214117 (1-[4-[6-methyl-5-(3,4,5-trimethoxyphenyl)-3-pyridinyl]phenyl] piperazine), ML347 (5-[6-(4-methoxyphenyl) pyrazolo[1,5-α]pyrimidin-3-yl]quinoline), an ALK3 antisense nucleic acid or siRNA, and a BMP4 antisense nucleic acid or siRNA, wherein the disease involving retinal ganglion cell death is selected from the group consisting of glaucoma, retinal vascular occlusion, ischemic optic neuropathy, and Leber disease, and wherein the fragment is at least one selected from the group consisting of a Fab, a F(ab')2, a Fv, a scFv, a scFv-Fc, a minibody, and a diabody.

5. The method according to claim 4, wherein the ALK3 signal transduction inhibitor is at least an anti-ALK3 antibody or a fragment thereof that binds ALK3.

6. The method according to claim 4, wherein the ALK3 signal transduction inhibitor is at least an anti-BMP4 antibody or a fragment thereof that binds BMP4.

7. The method according to claim 4, wherein the ALK3 signal transduction inhibitor is at least one selected from the group consisting of LDN-193189 (4-6-(4-piperazin-1-yl-phenyl)-pyrazolo[1,5-α]pyrimidin-3-yl]-quinoline), 2-(3-(6-methylpyridin-2-yl)-1H-pyrazol-4-yl)-1,5-naphthyridine, K02288 (3-[6-amino-5-(3,4,5-trimethoxyphenyl)-3-pyridinyl]-phenol), DMH-1 (4-[6-[4-(1-methylethoxy)phenyl] pyrazolo[1,5-α]pyrimidin-3-yl]-quinoline), LDN-212854 (5-(6-(4-(1-piperazinyl)phenyl)pyrazolo[1,5-α]pyrimidin-3-yl)quinoline), LDN-214117 (1-[4-[6-methyl-5-(3,4,5-trimethoxyphenyl)-3-pyridinyl]phenyl] piperazine), and ML347 (5-[6-(4-methoxyphenyl)pyrazolo[1,5-α]pyrimidin-3-yl]quinoline).

8. The method according to claim 4, wherein the ALK3 signal transduction inhibitor is at least an ALK3 antisense nucleic acid or siRNA.

9. The method according to claim 4, wherein the ALK3 signal transduction inhibitor is at least a BMP4 antisense nucleic acid or siRNA.

10. The method according to claim 4, wherein the disease involving retinal ganglion cell death is glaucoma.

11. The method according to claim 10, wherein the ALK3 signal transduction inhibitor is at least an anti-ALK3 antibody or a fragment thereof that binds ALK3.

12. The method according to claim 10, wherein the ALK3 signal transduction inhibitor is at least an anti-BMP4 antibody or a fragment thereof that binds BMP4.

13. The method according to claim 10, wherein the ALK3 signal transduction inhibitor is at least one selected from the group consisting of LDN-193189 (4-[6-(4-piperazin-1-yl-phenyl)-pyrazolo[1,5-α]pyrimidin-3-yl]-quinoline), 2-(3-(6-methylpyridin-2-yl)-1H-pyrazol-4-yl)-1,5-naphthyridine, K02288 (3-[6-amino-5-(3,4,5-trimethoxyphenyl)-3-pyridinyl]-phenol), DMH-1 (4-[6-[4-(1-methylethoxy)phenyl] pyrazolo[1,5-α]pyrimidin-3-yl]-quinoline), LDN-212854 (5-(6-(4-(1-piperazinyl)phenyl)pyrazolo[1,5-α]pyrimidin-3-yl) quinoline), LDN-214117 (1-[4-[6-methyl-5-(3,4,5- trimethoxyphenyl)-3-pyridinyl]phenyl] piperazine), and ML347 (5-[6-(4-methoxyphenyl)pyrazolo[1,5-α]pyrimidin-3-yl]quinoline).

14. The method according to claim 10, wherein the ALK3 signal transduction inhibitor is at least an ALK3 antisense nucleic acid or siRNA.

15. The method according to claim 10, wherein the ALK3 signal transduction inhibitor is at least a BMP4 antisense nucleic acid or siRNA.

* * * * *